United States Patent [19]
Rosenfield

[11] Patent Number: 6,004,751
[45] Date of Patent: Dec. 21, 1999

[54] IDENTIFICATION OF ACTIVATORS AND INHIBITORS OF SEBUM FORMATION

[75] Inventor: Robert L. Rosenfield, Chicago, Ill.

[73] Assignee: Arch Development Corporation, Chicago, Ill.

[21] Appl. No.: 08/917,653

[22] Filed: Aug. 22, 1997

Related U.S. Application Data

[60] Provisional application No. 06/028,618, Aug. 23, 1996.
[51] Int. Cl.⁶ ....................................................... C12N 5/00
[52] U.S. Cl. .................................................. 435/6; 435/325
[58] Field of Search .......................................... 435/325, 6

[56] References Cited

U.S. PATENT DOCUMENTS

| | | |
|---|---|---|
| 5,369,126 | 11/1994 | Doran et al. . |
| 5,690,948 | 11/1997 | McCook et al. . |
| 5,762,947 | 6/1998 | Guerrero et al. . |
| 5,773,015 | 6/1998 | Bajor et al. . |

*Primary Examiner*—Leon B. Lankford, Jr.
*Attorney, Agent, or Firm*—Arnold, White & Durkee

[57] ABSTRACT

The present invention relates to sebum formation in culture. More particularly, it relates to methods for the identification of compounds that stimulate and inhibit sebum formation in sebocyte culture. Further, it discloses methods for the treatment of conditions relating to excess or deficient sebum formation.

10 Claims, 14 Drawing Sheets

*P <.001 vs all
†P <.05 vs one another

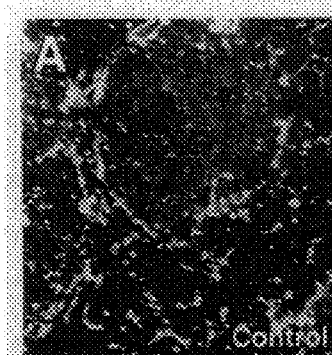
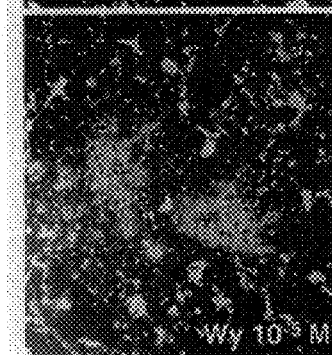
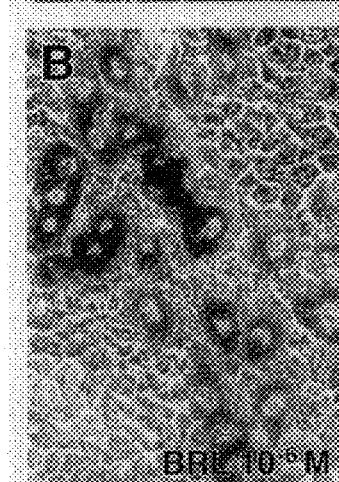
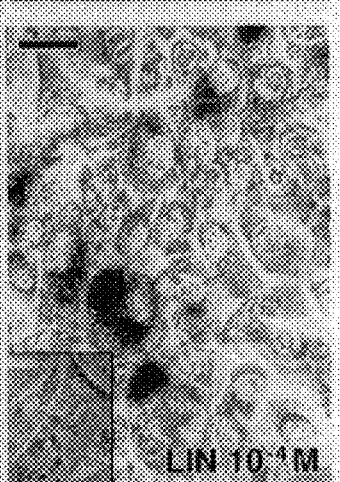
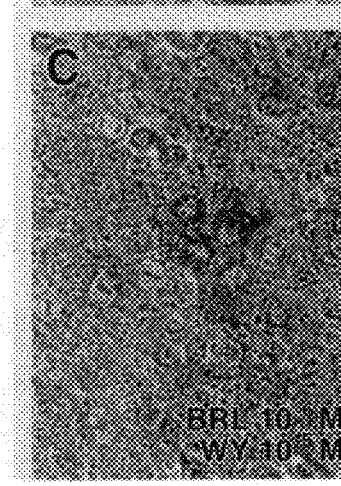
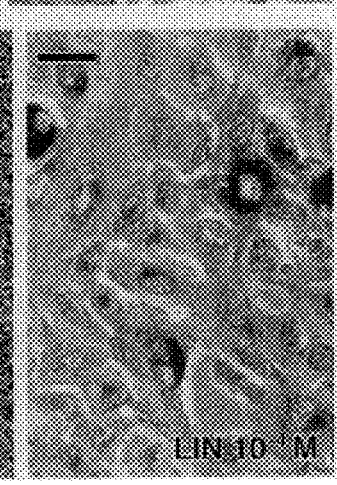
FIG. 9A
FIG. 9B
FIG. 9C
FIG. 9D
FIG. 9E
FIG. 9F
FIG. 9G
FIG. 9H

```
mPPARgamma2  CCCAGTGTGA ATTACAGCAA ATCTCTGTTT TATGCTGT
rPPARgamma2  ---------- ---------- ---------- -------- mPPARgamma2  GAGCATGGTG CCTTCGCTGA TGCACTGCCT ATGAGCACT
rPPARgamma2  GAGCATGGTG CCTTCGCTGA TGCACTGCCT ATGAGCACT mPPARgamma2  TTCTGGCCCA CCAACTTCGG AATCAGCTCT GTGGACCTC
rPPARgamma2  TTCTGGCCCA CCAACTTCGG AATCAGCTCT GTGGACCTC mPPARgamma2  CAAG CCCTTT ACCA AGTTG ATTTCTCCAG CATTTCTG
rPPARgamma2  -AAA- CCCTTT ACCA GGTTG ATTTCTCCA- CATTTCTG mPPARgamma2  ACCCAATGGT TGCTGAT TAC AAATATGACC TGAAGCTCC
rPPARgamma2  ACCCAATGGT TGCTGAT  --- ---------- --------
```

FIG. 10-1

| FIG. 10-1 |
|-----------|
| FIG. 10-2 |

FIG. 10

```
A  TGGGTGAAAC TCTGGGAGAT TCTCCTGTTG ACCCA    75
A  TGGGTGAAAC TCTGGGAGAT CCTCCTGTTG ACCCA    37

T  CACAAGAAAT TACCATGGTT GACACAGAGA TGCCA   150
T  CACAAGAAAT TACCATGGTT GACACAGAGA TGCCA   112

T  CGTGATGGA  AGACCACTG  C-ATTCCTTT GACAT   224
T  CTGTGATGGA TGACAACTCC CAATTCCTTT GACAT   187

CT CCACACTATG AAGACAT    ICCATTCACAAGA-GCTG  298
CT CCACACTATG AAGACAT    CCGTTCACAAGAAGCTG   260

A  AGAATACCAA AGTGCGATCA AAGTAGAACC TGCAT   373
-  ---------- ---------- ---------- -----   277
```

FIG. 10-2

IDENTIFICATION OF ACTIVATORS AND INHIBITORS OF SEBUM FORMATION

The present application is a continuation-in-part of U.S. Provisional Patent Application Ser. No. 60/028,618 filed Aug. 23, 1996. The entire text of the above-referenced disclosure is specifically incorporated by reference herein without disclaimer. The government owns rights in the present invention pursuant to grant number RO1-HD-06308 from the U.S. Public Health Service.

BACKGROUND OF THE INVENTION

1. Field of the Invention

The present invention relates generally to the field of lipid biochemistry. More particularly, it concerns methods for identification of compounds that stimulate sebum formation, identification of compounds that suppress sebum formation and uses thereof.

2. Description of Related Art

It has long been known that sebaceous gland function in man, and many other animals, is androgen dependent. Many studies have suggested a relationship between the rate of sebum excretion and the severity of androgen dependent disorders. A clear manifestation of this effect of androgens is seen at puberty, where there is an increase in androgen levels in man and a concurrent increase in androgen related acne formation. However it seems that androgen alone is not enough to stimulate sebum formation and some other factor is necessary for androgen to stimulate sebum formation.

Sebum is the holocrine excretion of the sebaceous cell (sebocyte). The maturation of the sebocyte is characterized by lipid production. Histologic evidence indicates that mitotic activity occurs mostly in undifferentiated cells, and that epithelial buds can grow from these cells at any point and differentiate into new acinar units (Brown and Williams, 1972).

From this it has been surmised that once a sebocyte begins to differentiate, it is committed to autolysis. However, the maturational stage at which sebocytes are committed to die has not been experimentally determined in a biologic system. Since maturing sebocytes differentially regulate protein, lipid, and steroid metabolism (Wheatley et al., 1979; Brind et al., 1984; Alves et al., 1986), they may well retain the capacity to proliferate. In support of this concept, the proliferative ability to early differentiating cells on the basis of light microscopy (Plewig et al., 1971).

There have been many attempts to study sebocytes in culture (Wheatley and Brind, 1981). However, studies have been hampered by the limited viability of these cells in culture. Typically the effects of hormones and drugs could only be evaluated in incubations of under 3 hours. Nevertheless, lipogenesis in sebocytes has been found to be stimulated by epinephrine, cyclic adenosine monophosphate (cAMP), and prostaglandin $E_2$, and it was inhibited by levodopa as well as antilipemic drugs such as nicotinic acid and clofibrate. However, no effect could be elicited from androgens or retinoic acid, apparently because the time-span of hormone exposure was too short to elicit a cellular response.

In the absence of a culture system, the most widely used bioassay system to detect the effects of drugs on sebaceous gland development utilizes the hamster flank organ. This assay is performed in the intact animal and has a major drawback in that androgen application suffices to produce an adequate response in the presence of factors already present within the intact animal. Hence this animal bioassay is completely ineffective for use in determining those factors that augment the effects of androgen in sebum differentiation. Therefore, a clear need exists for a viable cell culture system for the study of sebaceous gland development life cycle and to determine those factors that regulate their maturation and necrosis requires a technique for culturing these cells.

Acne vulgaris is the most common skin disorder in humans. It does not occur in the absence of the increased amounts of androgen that are produced at puberty. Acne results from a combination of increased sebum production, outlet (infundibulum) plugging and secondary infection. It appears that more than androgen is involved in regulating the growth and development of the preputial gland, as in human sebaceous glands (Wheatley, 1986; Thody and Shuster, 1989). This is borne out by several observations: (a) acne wanes after puberty in spite of stable androgen levels; (b) variable expression of androgen action on sebaceous components of pilosebaceous units (PSU) of different body areas (e.g., "beard area" versus "acne area"); (c) variable PSU expression of androgen excess as acne, hirsutism or baldness (Rosenfield, 1986); and (d) failure of androgen to induce substantial sebocyte differentiation in culture. There have been numerous disparate studies as to the identity of the factor that acts with androgen to stimulate sebum production, sebocyte differentiation and ultimately cell death. For example, retinoids cause atrophy and decreased lipid production (Boris et al., 1988; Gomez and Martinez, 1982), antagonizing the effects of testosterone, while catechols stimulate lipogenesis (Wheatley and Brind, 1981).

The reasons set forth above clearly demonstrate the need to elucidate those factors and mechanisms responsible for the stimulation of sebum formation and to find compounds to counteract such stimulation and thereby alleviate the symptoms of sebum formation or indeed to prevent such symptoms form appearing. In order to accomplish these tasks, it is imperative to establish a stable model for the differentiating sebaceous gland.

SUMMARY OF THE INVENTION

The present invention addresses these and other drawbacks in the prior art by providing a system for the study of sebocyte development and formation in culture. The culture system provides a model system in which sebocytes become fully differentiated in the presence of androgen and a non-androgen stimulator. The present invention has identified factors that serve to stimulate sebum formation such a as peroxisome proliferators and, hence, for the first time a model of the sebaceous gland development in culture is available. This system affords the possibility of identifying agents for diagnosis and treatment of disorders of sebum formation and sebocyte differentiation.

Thus, there is provided in accordance with the present invention, a method for the identification of a candidate substance that is a non-androgenic stimulator of sebum formation in culture comprising the steps of (i) providing at least one sebocyte; (ii) contacting said sebocyte with an androgen composition and said candidate substance; (iii) culturing said sebocyte; and (iv) determining the formation of sebum in said sebocyte, wherein the presence of sebum indicates that said candidate substance acts with androgen in formation of sebum. The method may further comprise a plurality of sebocytes, wherein said culture is a monolayer culture. The method may employ and androgen composition that comprises testosterone, 5α-dihydrotestosterone, ethyltestosterone, dehydroepiandrosterone, dehydroepiandrosterone sulfate, methyltestosterone, androsteredione, androstanediols, estradiol, mibolerone or fluoxymesterone or analogs thereof. Where dihydrotestosterone is used, it is effectively used in a concentration between about $10^{-5}$M and about $10^{-9}$M, and more preferably, in a concentration of about $10^{-6}$M. Methods of detecting sebum formation can comprise light microscopy, electron microscopy, fluorescence microscopy, flow cytofluorometry, immunoassays or chromatographic techniques.

Based on the data presented herein, one also may conduct the method described above while dispensing with the androgen composition, at least using certain non-androgen stimulators at sufficient concentrations.

In another embodiment, there is provided a method for the identification of a candidate inhibitor substance that is an antagonist of sebum formation comprising the steps of (i) providing at least one sebocyte; (ii) contacting said sebocyte with an androgen composition, an nonadrogenic stimulator of sebum formation and a candidate inhibitor substance; (iii) culturing said sebocyte; and (iv) comparing the formation of sebum in said sebocyte with the formation of sebum in a sebocyte cultured with said androgen composition and said stimulator, but in the absence of said candidate inhibitor substance. The method may further comprise a plurality of sebocytes, wherein said culture is a monolayer culture. The non-androgen stimulator may be a peroxisome proliferator, for example, a prostaglandin $J_2$ metabolite, thiazolidinediones, such as troglitazone, growth hormone, pyrinixic acid, tetrazole-substituted acetophenone or fibrate. WY 14643 is an exemplary fibrate, BRL-49653 is an exemplary thiazolidinedione and LY-171883 is an exemplary tetrazole-substituted acetophenone for use in the present invention. The androgen composition may comprise testosterone, 5α-dihydrotestosterone, ethyltestosterone, dehydro-epiandrosterone, dehydroepiandrosterone sulfate, methyltestosterone, androsteredione, androstanediols, estradiol, mibolerone or fluoxymesterone or analogs thereof.

In yet another embodiment, there is provided a method for the inhibition of sebum formation in a subject comprising providing an inhibitor of peroxisome proliferation in an amount effective to reduce sebum formation in said subject. Such methods may be used to treat acne in a human subject. The inhibitor of peroxisome proliferation may be an inhibitor of prostaglandin $J_2$ or prostacyclin activity, such as a retinoid or biosynthesis. Administration may be in the form of a topical application to said subject or a systemic administration to said subject.

In still yet another embodiment, there is provided a pharmaceutical composition comprising an inhibitor of peroxisome proliferation in an amount effective to reduce sebum formation. The pharmaceutical composition may be a topical composition or an oral composition.

In still yet another embodiment, there is provided a pharmaceutical composition comprising a peroxisome proliferator in an amount effective to increase sebum formation. The pharmaceutical composition may be a topical composition or an oral composition.

In still yet another embodiment, there is provided an agent that synergizes with androgen to stimulate sebum formation identified according to a method comprising the steps of (i) providing at least one sebocyte; (ii) contacting said sebocyte with an androgen composition and said candidate substance; (iii) culturing said sebocyte; and (iv) determining the formation of sebum in said sebocyte, wherein the presence of sebum indicates that said candidate substance synergizes with androgen in formation of sebum.

In still yet another embodiment, there is provided a candidate substance that is an antagonist of sebum formation identified according to a method comprising the steps of (i) providing at least one sebocyte; (ii) contacting said sebocyte with an androgen composition, a non-androgen stimulator and a candidate inhibitor substance; (iii) culturing said sebocyte; and (iv) comparing the formation of sebum in said sebocyte with the formation of sebum in a sebocyte cultured with an androgen composition and a non-androgen stimulator, but in the absence of a candidate inhibitor substance.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A—The prostaglandin biosynthetic pathway. FIG. 1B—The general eicosanoid metabolism pathway. FIG. 1C -5-, 12-, 15-LO interaction generating lipoxins.

FIG. 2: The effects of thiazolidinedione±DHT on sebocyte differentiation in vitro. Varying concentrations of BRL-49653 ($10^{-10}$M to $10^{-6}$M) alone and in combination with $10^{-6}$M DHT are shown.

FIG. 3 The effects of diverse treatments on sebum formation in cell culture. The effects of BRL-49653, WY-14643, LY-171883, indomethacin, dapsone and dapsone+BRL-49653 are shown.

FIG. 5. Differentiation of preputial sebocyte colonies in response to various doses of BRL with and without DHT (n=5). Percent of colonies with 6–50 or >50 Oil Red O (ORO)-staining cells is shown; means+SEMs are shown for the sum of both groups (lipid-forming colonies, LFCs). BRL has a dose-response effect over broad range commencing at $10^{-10}$ M (p <0.01 vs control, with $10^{-8}$ M BRL differing from the higher and lower doses at the p level shown). DHT is additive in its effect with BRL $\geq 10^{-8}$ M. DHT has a small but significant effect (p <0.05), and the effect of DHT+BRL $10^{-6}$ M is greater than that of all other treatments. *p<0.05 vs all other groups.

Figure 6A:
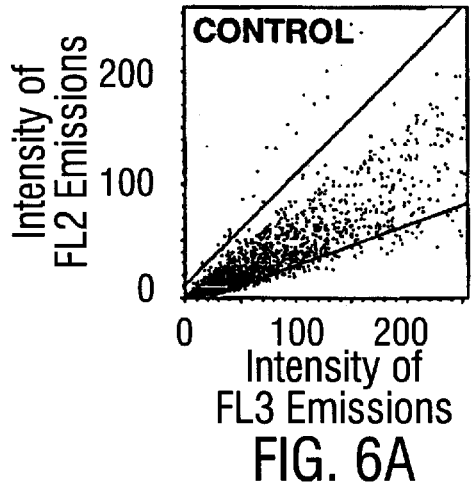
FIG. 6A, FIG. 6B, FIG. 6C and FIG. 6D. Quantitation of neutral lipid in cultured preputial cells by fluorescence-activated cell scanning. Results of a representative study are shown in which cultured cells were dispersed, incubated with Nile Red, and fluorescence emission was evaluated for the yellow-gold band characteristic of neutral lipids (FL2)
Figure 6B:
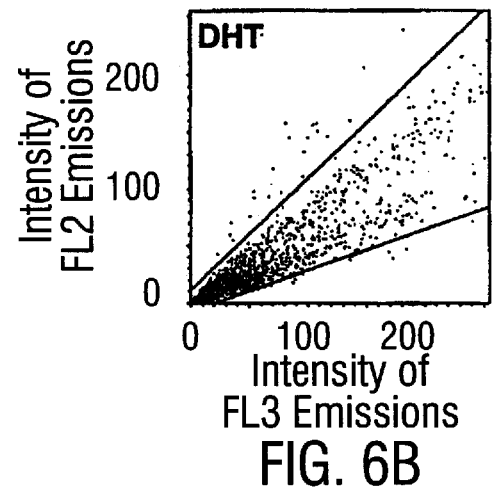
Figure 6C:
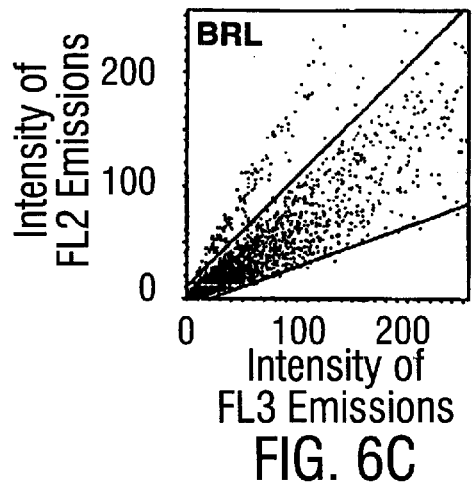
Figure 6D:
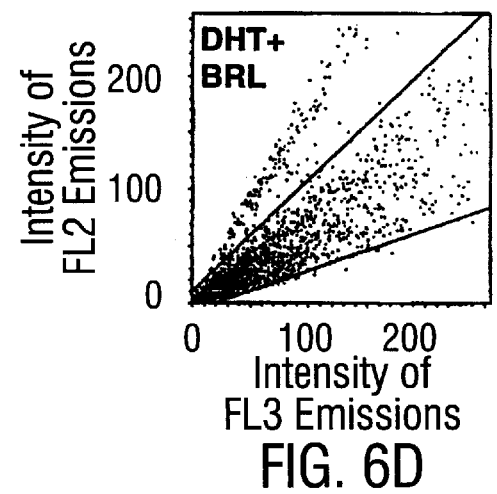

and for the red band characteristic of amphipathic lipids (FL3). The neutral lipid fluorescence of cells is seen above the upper gate, and it can be seen to successively increase with control (FIG. 6A), DHT (FIG. 6B), BRL (FIG. 6C), and DHT plus BRL (FIG. 6D) treatments.

Figure 7:
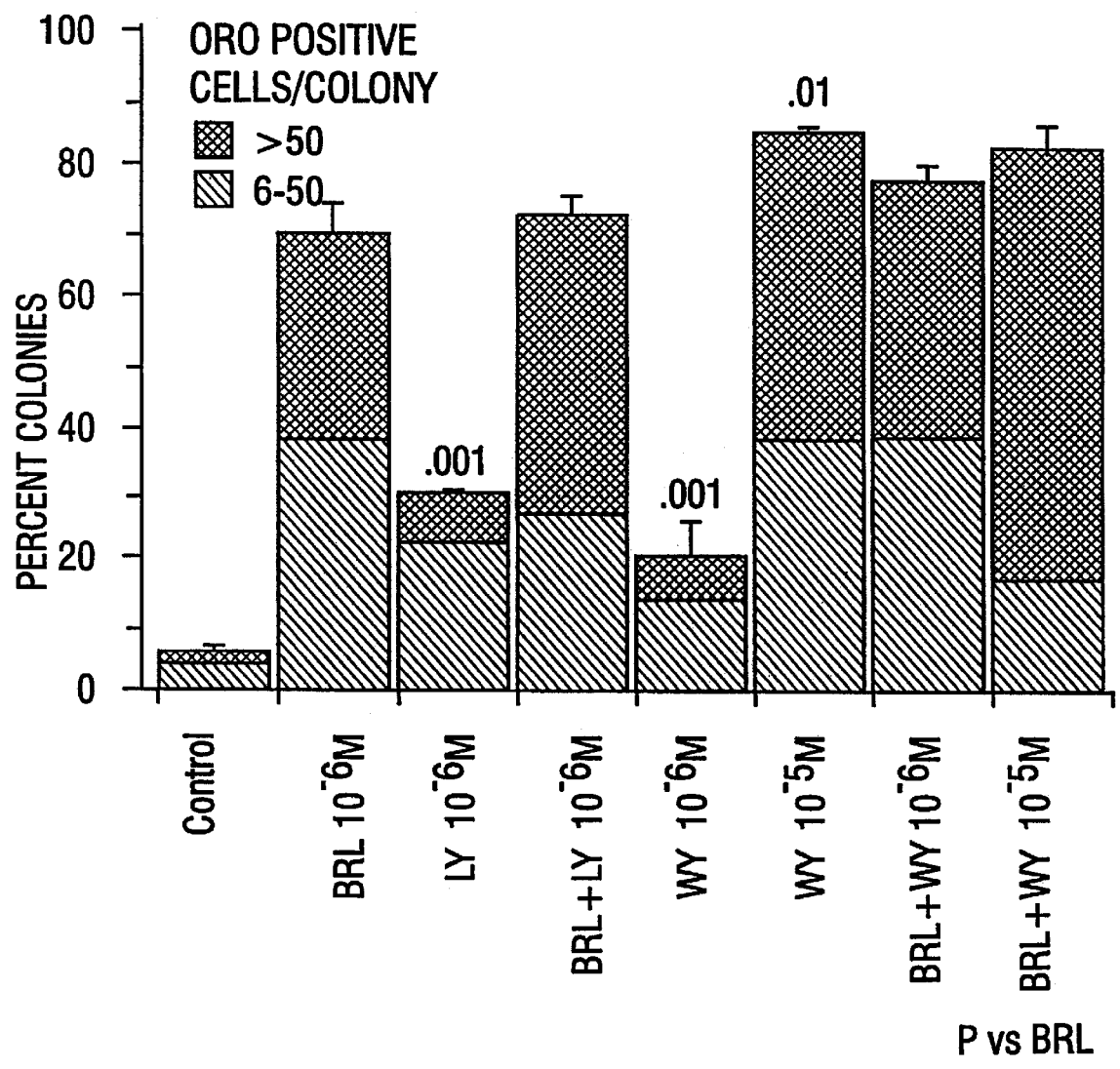

FIG. 7. Differentiation of preputial sebocyte colonies in response to LY or WY, with and without BRL (n=5). Both LY and WY stimulate sebum formation, but are less potent than BRL.

Figure 8:
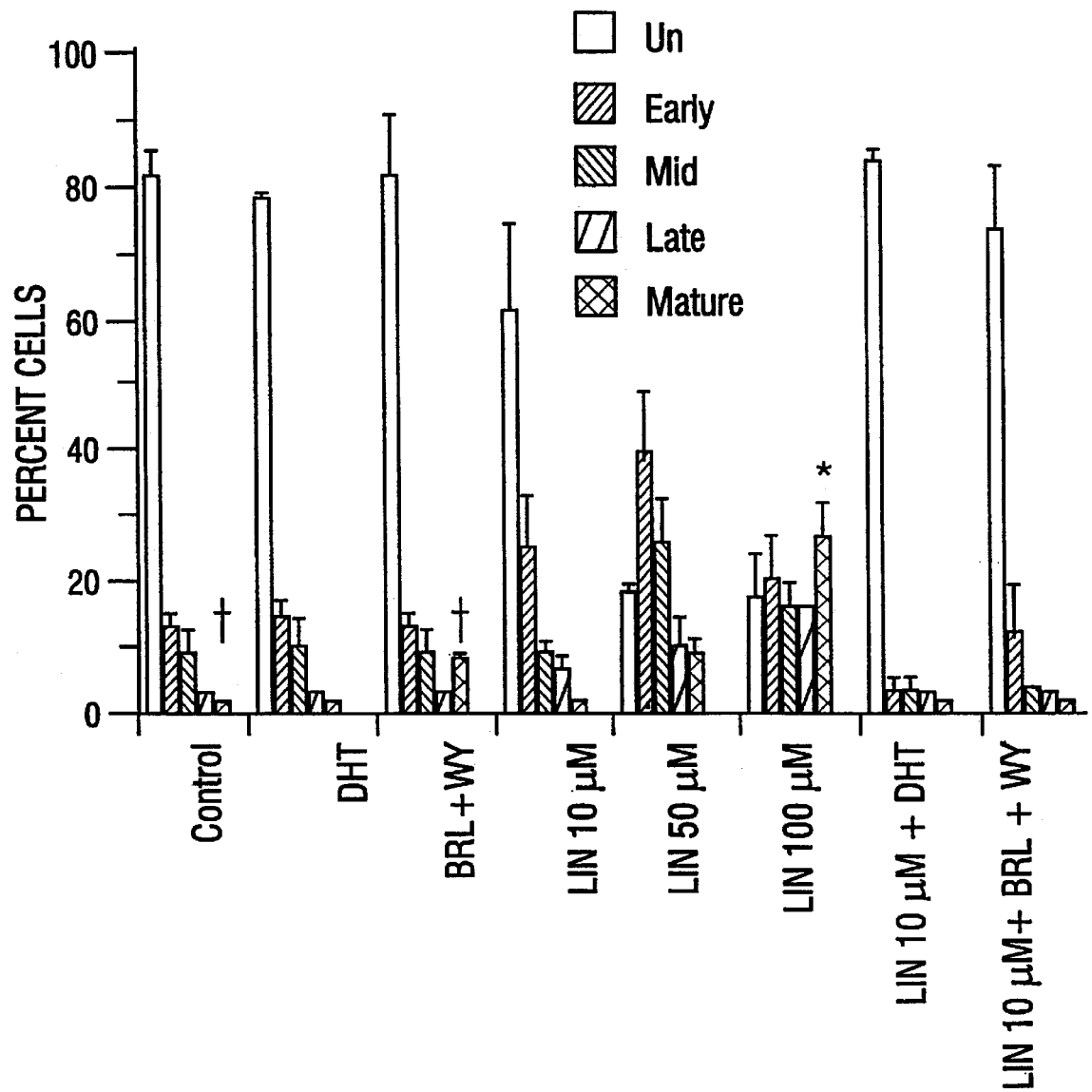

FIG. 8. Differentiation of preputial sebocytes in response to linoleic acid (LIN). LIN $10^{-4}$ M is more effective in stimulating full maturation of sebocytes than any other PPAR activator, alone or in combination (n=3). Percent of cells et each successive stage of maturation from undifferentiated (UN) to mature (Rosenfield, 1989) are shown. The percent mature cells was significantly greater after LIN 100 $\mu$M than after any other treatment (*), and the percent late-differentiated cells was higher after LIN 50–100 $\mu$M than after DHT $10^{-6}$ M or BRL $10^{-6}$ M plus WY $10^{-5}$M (P<.001).

FIG. 9A, FIG. 9B, FIG. 9C FIG. 9D, FIG. 9E, FIG. 9F, FIG. 9G and FIG. 9H. Effect of PPAR activators on epithelial cell morphology in monolayer culture. Oil Red O (ORO) stain. FIG. 9A–FIG. 9D Scanning power view of sebocyte colonies in response to PPAR activators. BRL (FIG. 9B) and WY (FIG. 9C) treatments cause lipids (reddish gold stain) to accumulate in the center of colonies, but LIN treatment (FIG. 9D) causes lipid staining throughout colonies and the colony morphology is looser, Bar=400 $\mu$m. FIG. 9E–FIG. 9F High power view of preputial cells after treatment with BRL (FIG. 9E) and LIN (FIG. 9F). BRL treatment (like WY) leads to lipid accumulation in only a small fraction of sebocytes. In contrast, most sebocytes differentiate upon treatment with LIN, the spectrum ranging from perinuclear lipid droplets in healthy cells to disintegrating mature sebocytes, LIN also induced lipid formation in the 3T3-cell feeder layer (Inset). Bar=50 $\mu$m. FIG. 9G–FIG. 9H High power view of cultured epidermal cells after treatment with BRL+WY (FIG. 9G) and LIN (FIG. 9H). On BRL plus WY, epidermal cells contain at most a few amorphous accumulations of lipid. Only LIN stimulates lipid droplet accumulation in cultured epidermal cells, which suggests that long chain fatty metabolites or PPARδ are normally involved in formation of epidermal cell lipids. Bar=50 $\mu$m.

FIG. 10. Homology between rat (SEQ ID NO:4) and mouse (SEQ ID NO:3) PPARγ in the A/B domain. There is 95% homology (boxed) between the mouse and rat cDNAs in this area of DNA. The start codon for γ2 is at bp39 and for γ1 is at bp129 of the mouse PPAR.

Figure 11:
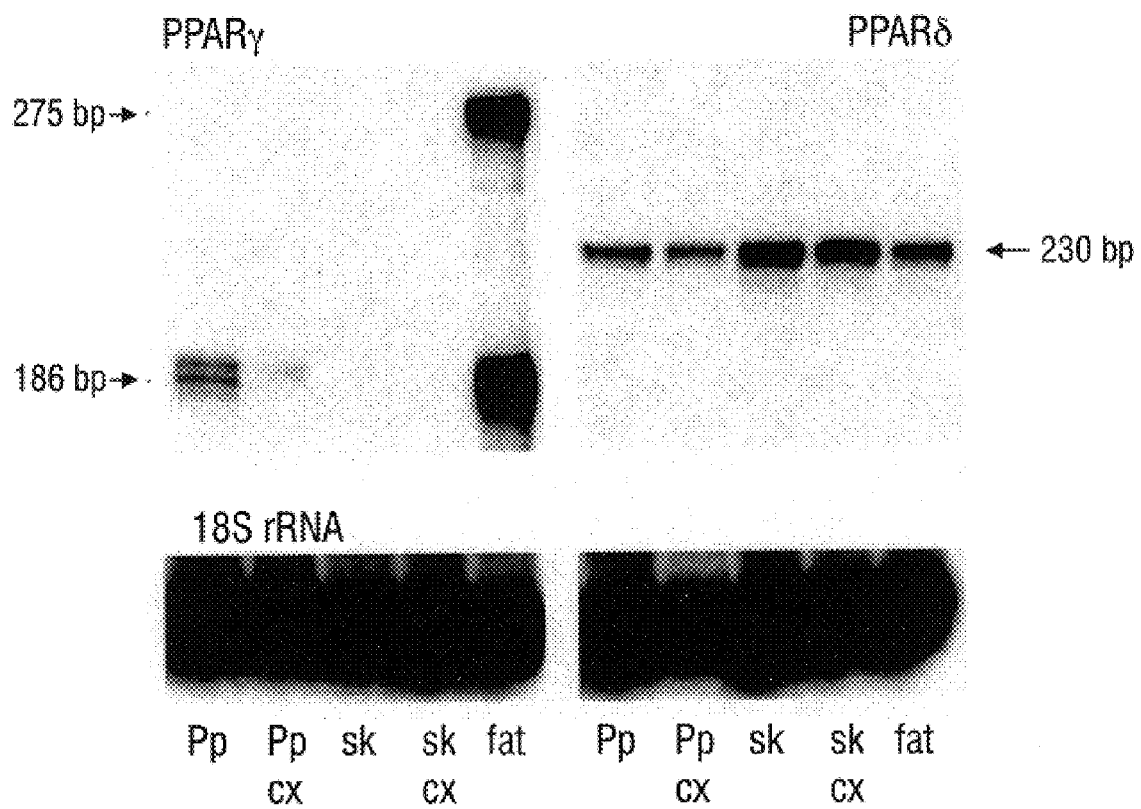

FIG. 11. PPARγ and PPARδ expression in rat tissues according to RNase protection assay. PPARγ is expressed in dispersed rat preputial sebocytes (Pp), Sebocytes express only the γ1 isoform (186 bps), in contrast to fat homogenates in which γ2 (275 bps) is also expressed. PPARγ is not found in dispersed epidermal cells (sk), PPARδ (230 bp) was expressed in all tissues, and more so in cultured (cx) Pp than PPARγ1, which can only faintly be seen.

DESCRIPTION OF ILLUSTRATIVE EMBODIMENTS

It is known that androgen plays an important role in sebum formation and the differentiation of sebocytes. It further is known that sebocytes do not differentiate completely with androgen alone and that some other factor(s) are needed for complete differentiation to occur. To date, it has not been possible to study the effects of androgen in a cell culture system due to the lack of viability of sebocytes in culture. In the absence of a viable cultured system for testing the effects of androgens and searching for other factors involved in sebocyte differentiation, the most widely used bioassay utilizes the hamster flank organ. This assay is performed in the intact animal and has a major drawback in that androgen application suffices to produce an adequate response due to factors already present within the intact animal. Hence, this animal bioassay is completely ineffective for use in determining those factors that augment the effects of androgen in sebum differentiation. Therefore, there is a clear need to provide model system for sebocyte development.

The present invention addresses these and other drawbacks in the prior art by providing a system for the study of sebocyte development and formation in culture. The culture system provides a model system in which sebocytes become fully differentiated in culture. The present invention has identified an additional factor required for the formation of sebum—a peroxisome proliferator. In some cases, this stimulator of sebum formation is sufficient, without the additional effect of androgen, to support sebocyte differentiation and sebum formation in vitro. Thus, for the first time, there is available a model of the sebaceous gland in culture. This system affords the possibility of identifying agents for diagnosis and treatment of disorders of sebum formation and sebocyte differentiation.

In one embodiment, the present invention details methods for identifying agents other than androgen that act cooperatively with, additively with, synergize with or induce androgen to stimulate sebum formation, herein referred to as "non-androgen stimulators of sebum formation." It is contemplated that such agents will be useful in the treatment of disorders manifesting a lack of sebum formation. These agents will be further useful in the diagnosis of disorders developing from an abundance of sebum formation, for example, acne vulgaris and acne rosacea.

In further embodiments, the present invention concerns immunodetection methods and associated kits. It is proposed that the non-androgen stimulators of the present invention may be employed to generate antibodies having reactivity therewith, or, alternatively, antibodies prepared in accordance with the present invention may be employed to detect non-androgen stimulators for diagnostic purposes or for analytical purposes in detection assays. In general, these methods will include first obtaining a sample suspected of containing such an non-androgen stimulator, contacting the sample with an antibody or peptide in accordance with the present invention, as the case may be, under conditions effective to allow the formation of an immunocomplex, and then detecting the presence of the immunocomplex.

For diagnostic purposes, it is proposed that virtually any sample suspected of comprising an non-androgen stimulator sought to be detected, may be employed. It is contemplated that such embodiments may have application in the diagnosing conditions where sebum formation has been produced due to androgen action in the presence of such non-androgen stimulators.

In a further aspect, the present invention provides methods of screening for and identifying agents that work against the action of androgen and/or non-androgen stimulators of sebum formation, herein referred to as antagonists of sebum formation. It is contemplated that such agents will be used for the treatment of disorders related to sebum formation such as for example, acne vulgaris and acne rosacea.

The identification and isolation of antagonists will yield active compounds which may be used for antibody production. Antibodies produced in such a manner are contemplated to be useful for the detection of non-androgen stimulators for use in ELISAs, RIAs and other methods requiring immunodetection, such methods are well known to those of skill in the art.

Another aspect of the present invention includes novel compositions comprising isolated and purified active non-androgen stimulators and antagonists of sebum formation. Pharmaceutical compositions prepared in accordance with the present invention find use in a variety of diagnostic and assay kits, as well as treatment of sebum formation disorders.

Therapeutic kits comprising non-androgen stimulator or antagonists comprise another aspect of the present invention. Such kits will generally contain, in suitable container means, a pharmaceutically acceptable formulation of the non-androgen stimulator or antagonist.

1. Sebocytes and Sebum Formation

Sebaceous glands can be grouped based on their location, their association with hair follicles and on their fimction. Sebaceous glands are found over most of the body and in man are especially concentrated in areas such as the scalp, forehead and face where there may be as many as 400–900 glands/cm$^2$. The majority of these glands are associated with hair follicles and are termed pilosebaceous units. Those glands not associated with hairs are known as free sebaceous glands and are particularly prevalent in transitional zones between the skin and mucus membranes.

Sebaceous glands form aggregates in some mammalian species, for example, ventral glands in gerbils, costovertebral glands of hamsters and caudal glands in guinea pigs. These glands may become encapsulated to form distinct organs as is the case with the preputial glands of mice and rats. These glands have specialized functions related to the secretion of odors or pheromones.

All sebaceous glands are similar in structure consisting of a single lobule (acinus) or a collection of lobules that open into a system of ducts as in the case of the pilosebaceous glands opening into the piliary canal. Conversely, free sebaceous glands open onto the skin surface. The glands are surrounded by a connective tissue capsule which separates the various acini and forms the collagenous stroma rich in fibroblasts and capillaries supporting the gland. The preputial glands also contain nerves. Sebaceous gland epithelial cells are divided into the lipid producing cells of the acinus and the stratified squamous epithelium cells of the duct. There also is an intercellular matrix of supporting fibroblastic cells which includes some monocytic cells.

The preputial glands are readily accessible, paired sebaceous glands located in the prepuce of rodents (Wheatley, 1986). They consist predominantly of sebaceous cells (sebocytes), with a few other cell types including duct cells. This sebaceous gland, like those of man, contains sebocytes in an encapsulated acinar arrangement at different maturational states (Wheatley, 1986; Thody and Shuster, 1989). Electron microscopy also shows the rodent and human glands to be similar in the morphology of organelles, such as abundant and sometimes atypical mitochondria, many perinuclear lysosomes with crystalline inclusions, peroxisomes and lipid droplets of various sizes (Ellis, 1968; Mednieks et al., 1991). Sebocytes are specialized epithelial cells which proliferate primarily in the undifferentiated and early differentiated cells located in the basal and parabasal layers (Mednieks et al., 1991; Jenkinson et al., 1985), as in skin. They differentiate into lipid-laden cells which rupture when fully mature, giving rise to the holocrine secretion, sebum.

Human sebum is mostly composed of triglycerides, wax esters and squalene, with smaller amounts of free fatty acids, sterols and steryl esters. At puberty sebaceous activity is greatly increased. There are many factors that affect the secretion of sebum. Endocrine mechanisms play a major role in the activity of sebaceous gland and evidence suggests that hormones play a role in the proliferation and lipogenic activity of sebocytes.

2. Peroxisome Proliferator Activated Receptors

The peroxisome proliferator activated receptors (PPARs) are nuclear hormone receptors that regulate gene transcription in response to peroxisome proliferators and fatty acids. PPARs also play an important role in the regulation of adipocyte differentiation. These receptors comprise a superfamily of transcription factors containing highly related DNA-binding domains (Evans, 1988; Green and Chambon, 1988). The family includes multiple subtypes of receptors for thyroxine and retinoids which are regulated differently during development and in adults (Lehman et al., 1992; Apfel et al., 1992). In addition, there are a large number of orphan receptors that have important roles in development (O'malley and Conneely, 1992).

The PPARs were initially cloned as orphan receptors and were subsequently found to be activated by peroxisome proliferators. Such proliferators include compounds such as clofibrate and WY14,643 which have been used clinically to treat hyperlipidemia as well as plasticizers (Issemann and Green, 1990). In mammals, there are multiple subtypes of PPARs called α, δ (or NUC-I) and γ. There are a number of studies that suggest that each of these subtypes is differentially activated by various compounds (Chen et al., 1993; Schmidt et al., 1992; Zhu et al., 1993; Kliewer et al., 1994; Dreyer et al., 1992). PPARα is most abundant in the liver, while the tissue distribution of PPARδ is more widespread. By contrast, the expression of PPARγ is limited to adipose tissues (Tontonoz et al., 1994a; Chawla et al., 1994a), indeed it has been shown that activators of PPAR can suffice to induce adipose conversion of preadipocyte cell lines (Brandes et al., 1977; Chawla et al., 1994b). Furthermore, ectopic expression of PPARγ causes fibroblast cell lines to differentiate in adipocytes in the presence of PPAR activators (Tontonoz et al., 1994b). Yu et al. (1995) suggest that the role of PPARs in adipocyte differentiation is likely to be complex since other PPARs are induced during adipocyte differentiation (Chawla et al., 1994b; Amri et al., 1995). It was found that PPARα, δ and γ had highly divergent properties with respect to activation by peroxisome proliferators and fatty acids. Further, they showed that prostaglandins A, D and J differentially activated PPAR subtypes, confirming that PPAR subtypes are pharmacologically distinct and that naturally occurring eicosanoids act as PPAR activators (Yu et al., 1995).

The present invention, for the first time, demonstrates the presence and role of PPARγ in sebaceous glands and sebocyte development. Further, the inventors demonstrate that androgen stimulates sebocyte differentiation by boosting PPARγ gene expression. Although BRL is a particularly potent inducer of lipid-forming colonies, all PPAR activators reproducibly induced sebocyte lipogenesis at concentrations which have been shown to strongly activate PPAR-reporter gene constructs. These results are further discussed herein below.

3. Effects of Androgens on the Sebaceous Gland

The development of the preputial gland, like that of human sebaceous glands, long has been known to be dependent on androgen action (Wheatley, 1986; Thody and Shuster, 1989). The preputial gland grows at puberty to achieve a weight of about 0.125 gm in the adult rat. This growth does not occur in the androgen-resistant rat (Sherins and Bardin, 1971; Yarbrough et al., 1990). Testosterone administration is known to stimulate preputial sebocyte proliferation (Ebling, 1973) and lipid production (Mesquita-Guimaraes and Coimbra, 1981), and antiandrogen reverses this effect (Ebling, 1973). As also appears to be the case in human sebaceous glands (Luu-The et al., 1994), testosterone is converted to the more potent androgen 5α-dihydrotestosterone (DHT) by the type 1 isoform of 5α-reductase rather than the type 2 isoform that predominates in the classic androgen target tissues of the genital tract.

Recent progress in human sebocyte research is pertinent to the developmental biology issues in preputial cell culture. Akamatsu et al. recently reported that human sebocyte proliferation in culture is stimulated by androgen (Akamatsu et al., 1992). DHT stimulated the growth of sebocytes from the face and thigh in a dose-dependent manner, with significant stimulation being observed at doses at $10^{-8}$ M or more. The antiandrogen spironolactone reversed the DHT effect (Akamatsu et al., 1993). Noteworthy was the fact that DHT did not stimulate differentiation.

The studies presented herein show that androgen alone had only a modest stimulatory effect on sebocyte differentiation in culture, here demonstrable for the first time upon omission of serum from the culture medium. The most prominent effect of androgen was to enhance the development of highly differentiated sebocyte colonies in response to the PPAR activator BRL-49653. Other factors also enhanced the sebocyte differentiation in combination with DHT, such agents include growth hormone. This suggests that androgen stimulates sebocyte differentiation by boosting PPARγ gene expression. The exact mechanism by which androgen does so remains to be elucidated. Sebocytes in monolayer culture produce very few lipid droplets, even in the presence of androgen. Thus, androgens alone cannot produce full sebocyte differentiation, so other factors are necessary for the expression of androgen action.

4. Sebocytes in Culture

The present invention for the first time details a culture system for studying the effects of androgen on sebocyte differentiation and determines the factors required for the manifestation of androgen effects on sebum formation. General culturing techniques are well known to those of skill in the art. The present invention provides a method of culturing sebocytes generally comprising obtaining and culturing a sebocyte; providing the sebocyte culture with a composition of androgen and further providing the sebocyte culture with a composition of a peroxisome proliferator that will act as a non-androgen stimulator and monitoring sebocyte differentiation. The androgen composition may be added prior to, after or concurrently with the peroxisome proliferator composition. In some cases, it may not be needed if the peroxisome proliferator is present in quantities sufficient to support sebocyte differentiation and/or sebum formation.

a. Peroxisome Proliferators i) Thiazolidinediones and other PPAR Activators

The present invention has shown that thiazolidinediones (TZL) are sebogenic. It was found that found that, at low concentrations (~$10^{-10}$M), TZL alone did not increase lipid droplet formation in cultured sebocytes, however, when TZL was added in combination with androgen or the concentration was increased, lipid droplet formation was increased.

Thiazolidinediones are a class of antidiabetic compounds have been shown to be adipogenic and have a high affinity for PPARγ ligands. Recently, it has been demonstrated in adipocytes that thiazolidinedione is a surrogate for a prostaglandin $J_2$ metabolite (Forman et al, 1995; Kliewer et al., 1995) which is natural peroxisome proliferator-activated receptor ligand. Although prostaglandins have been incriminated in mediating androgen action in sexual differentiation (Goldman et al, 1988), prostaglandins have never been suspected of being involved in sebocyte differentiation or the development of acne vulgaris.

The present invention clearly demonstrates that peroxisome proliferators such as TZL are stimulators with androgen in sebum formation and, in some cases, sufficient to support sebum formation alone. Other agents that activate peroxisome proliferation for use in the present invention include, but are not limited to, plasticizers, clofibrate, paglitazone, hypolipemic agents (e.g., pyrinixic acid (WY-14643; Biomol Research Laboratories, Plymouth Rock, Pa.)) LY-171883 (tetrazole-substituted acetophenone, a leukotriene D4 receptor antagonist; Biomol Research Laboratories). The methods set forth in the present invention will allow for the screening and detection of further peroxisome proliferators.

Although BRL is a particularly potent inducer of lipid-forming colonies, all PPAR activators reproducibly induced sebocyte lipogenesis at concentrations which have been shown to strongly activate PPAR-reporter gene constructs (Forman et al., 1997; Kliewer et al., 1994; Yu et al., 1995). At $10^{-6}$ M, BRL induced lipid formation in approximately 60%, WY in 19%, and LY in 28% of sebocyte colonies. However, linoleic acid at $10^{-4}$ M brought about the most complete differentiation of sebocytes. Over 95% of colonies differentiated into LFCs, and LIN was much more effective in inducing the late stages of sebocyte maturation. In addition, the degree of maturation, described in the examples herein, was more than reported in a human sebocyte secondary cell culture system (Zouboulls et al., 1994).

PPAR activators work by diverse mechanisms. Like other thiazolidinediones, BRL is a specific PPARγ ligand (Lehmann et al., 1995). WY is a hypolipemic clofibrate analog which is a PPARα ligand and which additionally activates PPARs indirectly by noncompetitively inhibiting several hepatic peroxisomal enzymes (Forman et al., 1997; Parthasarathy et al., 1982). In reporter systems it has 95% or more specificity for PPARα at concentrations up to $10^{-5}$ M, but at higher concentrations activates PPARγ equally well and has on occasion been reported to activate PPARδ up to 33% as well (Amri et al., 1995: Kliewer et al., 1995; Lehmann et al., 1995). Therefore, its greater effectiveness at $10^{-5}$M than BRL at $10^{-6}$ M may reflect some activation of PPARs other than PPARα. LY is a leukotriene D4 antagonist which activates PPARγ preferentially to PPARα (Forman et al., 1997; Foxworthy and Eacho, 1988; Lehmann et al., 1995). The lack of an additive effect of BRL with either of these agents suggests that PPARγ and PPARα transduce their effect(s) through a common pathway. LIN is a C18:2 fatty acid which is an informative activator of mammalian PPARs. It is a ligand of PPARδ and among the most potent activators of this PPAR subtype, while being one-tenth as potent in activating PPARγ and approximately equipotent in activating PPARα in reporter systems (Brun et al., 1996; Forman et al., 1997; Kliewer et al., 1994). The possibility that it simply exerts its effect by virtue of being an essential substrate for lipid metabolism seems unlikely since one-tenth of a maximally effective dose does not enhance the impressive BRL or WY efficacy which occurs in the absence of exogenous substrate. The greater effectiveness of LIN than the combination of maximally effective PPARγ and PPARα activators suggests that PPARδ activation is particularly important for the final stages of sebocyte lipogenesis and differentiation.

The PPAR activators led to distinct patterns of activation of sebocyte colonies. BRL, WY and $PGI_2$, alone or in combination, activated lipogenesis only in the central zone of colonies where the oldest cells of the colony reside, whereas LIN activated lipogenesis in sebocytes throughout colonies, even at the periphery of colonies where the youngest cells are proliferating. These observations are compatible with PPAR gene expression being developmentally regulated, since time in culture seems to be required for their induction. Since LIN is an essential fatty acid necessary for the synthesis of long chain fatty acids, it can be deduced that the latter are necessary for the final stage of sebocyte differentiation.

The inventors found PPARγ1 mRNA in abundance in freshly dispersed sebocytes, which are predominantly differentiated. However, PPARγ gene expression was detectable at only a low level in cultured sebocytes, which are predominantly immature (Rosenfield and Deplewki, 1995). PPARγ has not previously been detected in sebaceous glands (Braissant et al., 1996) probably because the methodology used was not as sensitive as the RNase protection assay used here. The inventors' molecular data are compatible with the concept that PPARγ gene expression is developmentally regulated. PPARγ1 gene expression appears to be minimal early in sebocyte differentiation and increases as sebocytes mature; the augmentation of BRL effectiveness by DHT suggests that androgen is one of the inducing factors. The induction of PPARγ1 gene expression may be an important regulated step which determines the transition from the early stage of sebocyte differentiation, at which perinuclear lipid droplets are submicroscopic, to the mid-differentiated stage, at which fused lipid droplets are visible microscopically.

The inventors' studies also demonstrate that PPARδ is constitutively expressed in both freshly dispersed and cultured sebocytes and epidermal cells, in contrast to PPARγ. PPARδ is known to be widely expressed, yet its activation has had no effect on fat cell differentiation (Brun et al., 1996), which has led to its physiologic relevance being questioned. The combination of strong activation of sebocyte differentiation by LIN and constitutive expression of relatively high levels of PPARδ suggests an important role for free fatty acids and PPARδ in the final stage of sebocyte terminal differentiation at which these cells burst and extrude lipid. Preputial gland lipids contain 3% free fatty acids and 56% triglycerides (Wheatley, 1986). However, preputial sebum triglycerides are lower and free fatty acid levels are 4-fold higher, reaching a millimolar concentration. This shift appears to be due to the presence of lipases of bacterial origin in the duct of the sebaceous gland. Thus, local increases in free fatty acids as sebocytes reach the sebaceous gland outlet may well serve to augment the final stages of sebocyte maturation.

Lipid formation by epidermal calls in response to LIN was initially unexpected, in part because PPARδ has not previously been detected in skin (Braissant et al., 1996). This was not found in response to any other PPAR activator. The inventors' demonstration of constitutive expression of PPARδ mRNA in skin keratinocytes lead the inventors to suggest that PPARδ is involved in formation of the lipids which epidermal cells export to maintain the epidermal water barrier and for which LIN is known to be required as an essential fatty acid (Schurer and Elisa, 1991; Swarzendruber et al., 1989). The unnatural prominence of lipid accumulation in cultured epidermal cells upon stimulation by LIN would seem explicable by the unphysiologic concentrations of free fatty acids to which the inventors have exposed these cells in culture.

Although the inventors' results indicate that lipogenesis in sebaceous epithelial cells is accomplished by some of the same gene mechanisms involved in adipocyte lipogenesis, the inventors' results contrast in certain ways that are likely to shed light on the differentiative processes of both types of cells. One important difference would seem to be the occurrence of sebocyte differentiation in the presence of cell proliferation, which contrasts with the situation in fat cells where synergism of PPARγ with CCAAT/enhancer binding protein α involves termination of mitosis (MacDonald and Lane, 1995; Spiegelman and Flier, 1996).

These findings also have implications for the therapy of acne vulgaris. Sebocyte differentiation is an important element in the pathogenesis of acne (Kligman, 1974), the most common skin disorder of adolescents (Phillips and Dover, 1992). The development of PPAR antagonists is worthwhile because of their potential advantages over currently available treatment modalities, which include suppression of androgen levels, use of anti-androgens, or use of retinoic acid analogs, all of which have major drawbacks.

ii) Prostaglandins

The prostaglandins (PG's) are a family of structurally related molecules that are produced by cells in response to a variety of extrinsic stimuli and are involved on the regulation of cellular growth, differentiation and homeostasis. PG's are derived from fatty acids, primarily arachidonic acid, which are released from membrane phospholipids by the action of phospholipases. Arachidonic acid is converted to an unstable endoperoxide intermediate by cyclooxygenase, and subsequently converted to one of several products. Included amongst these products is $PGD_2$. An alternate pathway of arachidonic acid conversion is by lipooxygenase, which leads to the formation of leukotrienes.

Figure 1A:
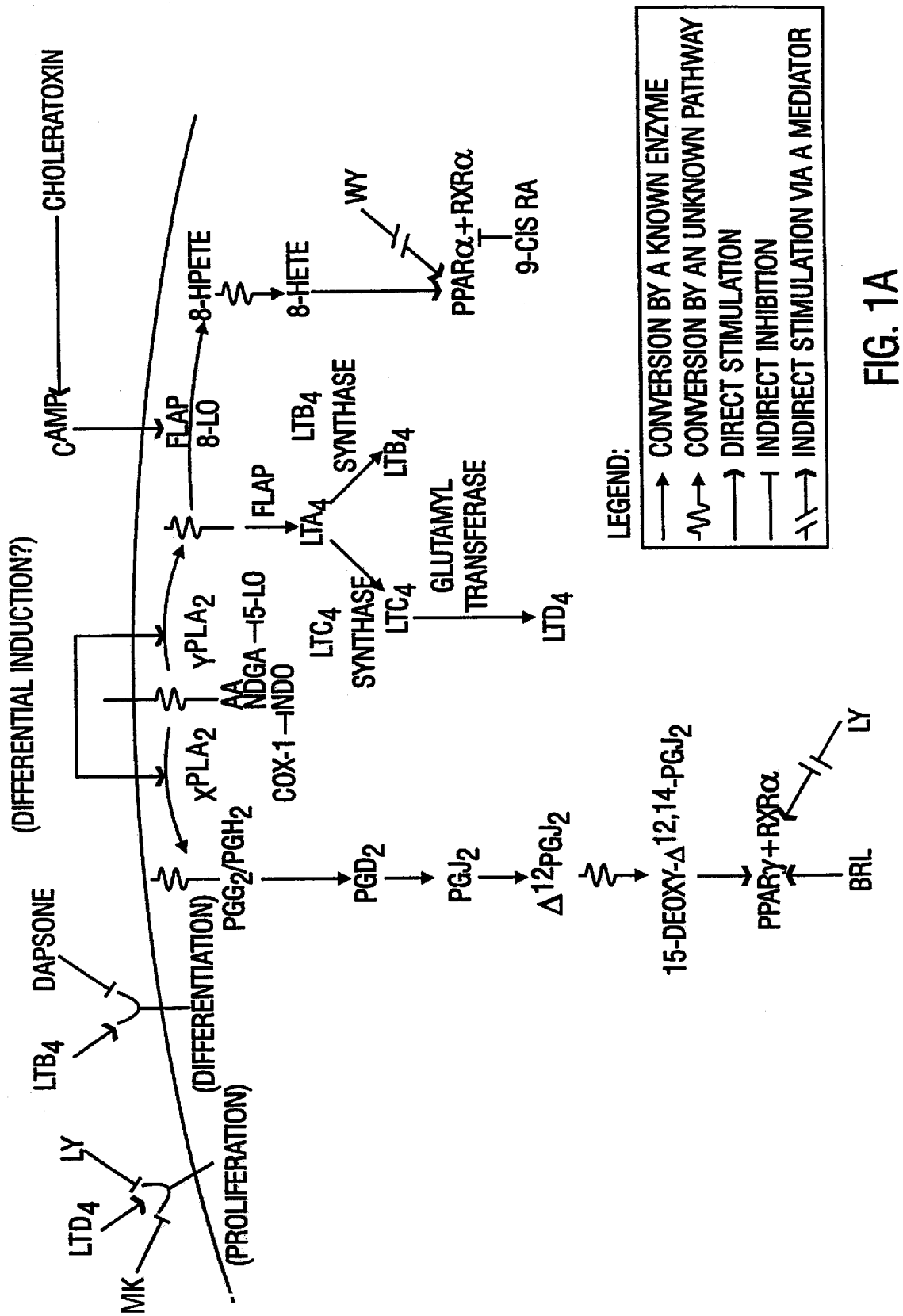
FIGS. 1A, FIG. 1B and FIG. 1C: Biosynthetic pathways.
Figure 1B:
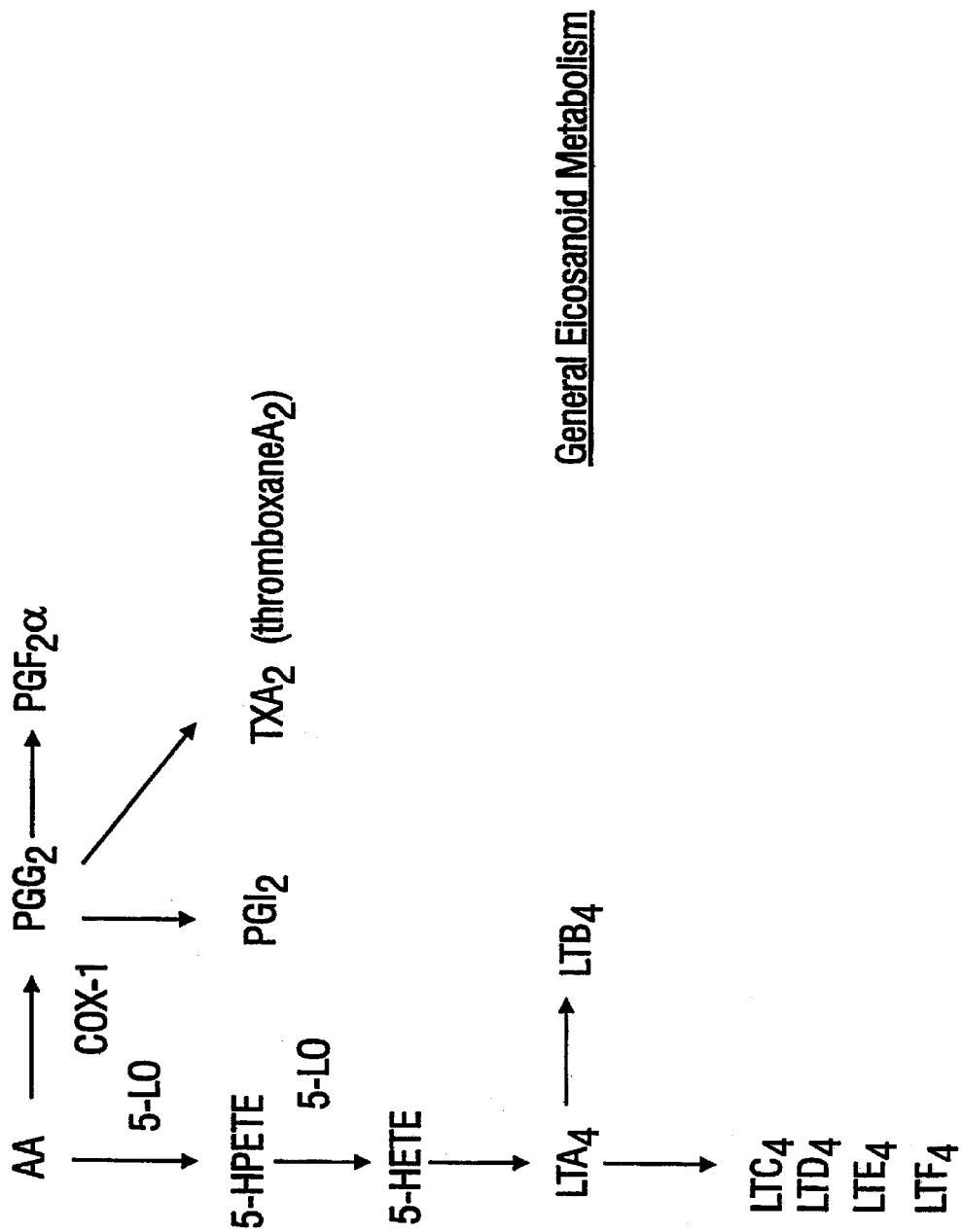
Figure 1C:
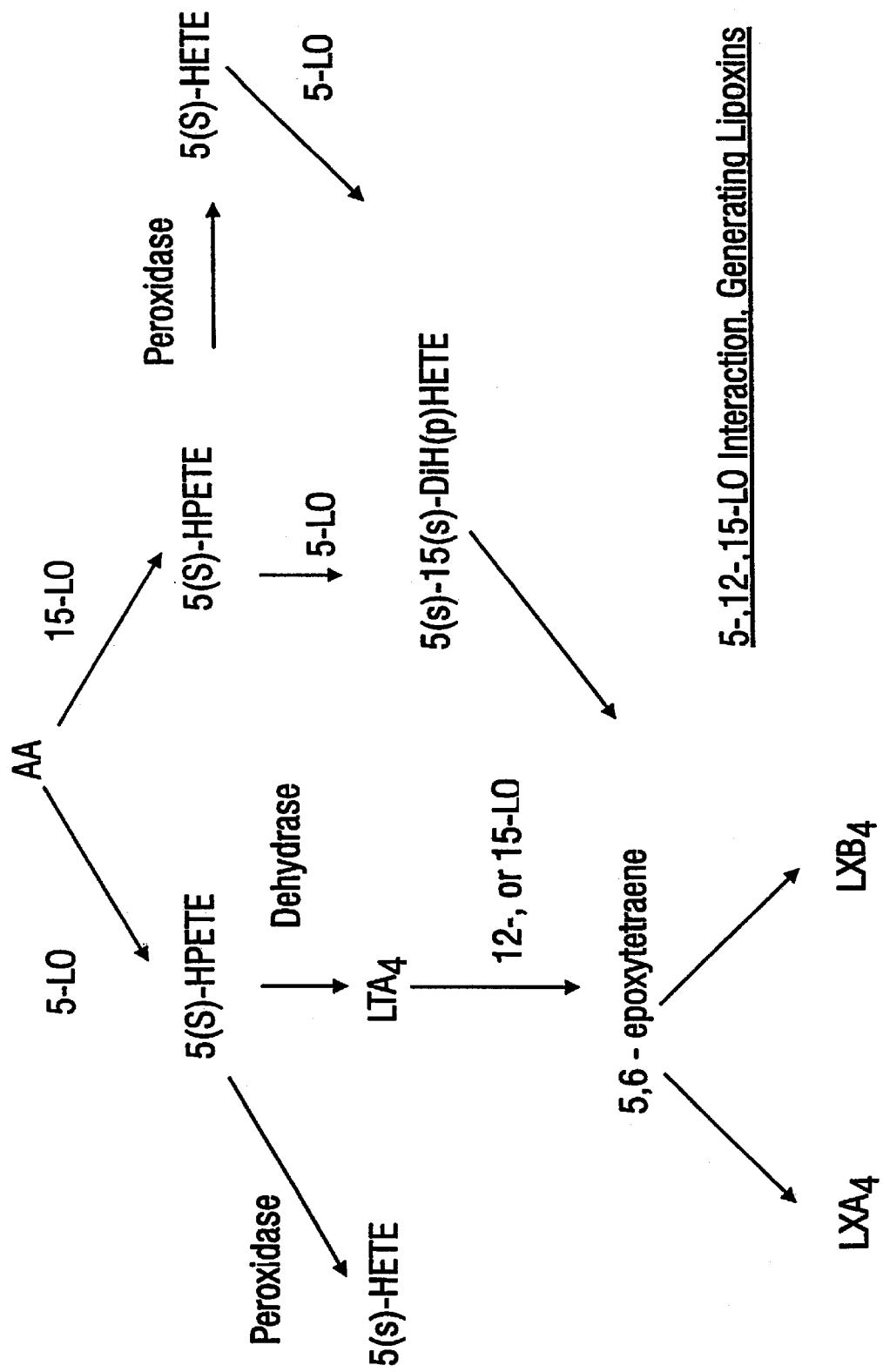

$PGD_2$ is a major product of cyclooxygenase in a variety of tissues and cells and affects numerous biological processes including platelet aggregation, relaxation of smooth muscle and nerve function (Giles and Leff, 1988). $PGD_2$ readily undergoes dehydration in vivo and in vitro to yield prostaglandins of the $J_2$ series ($PGJ_2$, FIG. 1A).

Members of the $PGJ_2$ series are known to have a spectrum of biological effects including inhibition of cell cycle progression, suppression of viral replication, induction of heat shock protein expression and stimulation of osteogenesis (Fukishima, 1992). The mechanism of action of $PGJ_2$ series prostaglandins is unknown. Recent studies have demonstrated that a $PGJ_2$ metabolite, deoxy$\Delta^{12,14}$-$PGJ_2$, is an adipogenic agent in fibroblasts. It has been suggested that this $PGJ_2$ metabolite binds to the peroxisome proliferating factor γ (PPARγ). As PPARγ is selectively expressed in adipocytes it raises the possibility of PG being involved in the differentiation of adipocyte.

Prostacyclin ($PGI_2$), a ligand an activator of all PPAR subtypes stimulates sebocytes to form lipid.

It has been shown that TZL is a surrogate of prostaglandin $J_2$. Hence the present invention contemplates the use of prostaglandin $J_2$ or prostacylin metabolites or derivatives thereof in synergizing the action of androgen in sebum formation. The purification and identification of prostaglandins is known to those of skill in the art. Such techniques generally involve the separation of desired compounds using chromatography separation techniques as described elsewhere in the specification.

b. Androgens

There are a wide variety of androgens, known to those of skill in the art, that may be used in conjunction with the present invention. Exemplary androgens of the present invention include, but are not limited to androstenediol, androstedione, androstanediols, dehydroepiandrosterone, dehydroepiandrosterone sulfate, dihydrotestosterone, testosterone, testosterone propionate, testosterone enanthate, testosterone cypionate, nandrolone decanoate, nandrolone phenpropionate, danazol fluoxymesterone, methandrostenolone, methyltestosterone, oxandrolone, oxymetholone, stanozolol, testolactone. These androgens are for use with active compounds of the present invention to stimulate sebum formation in sebocytes.

5. Assays for Non-Androgen Stimulators and Antagonists in Sebum Formation a. Stimulators of Sebum Formation The present invention provides methods of screening for non-androgen stimulators of sebum formation, as defined above, activity in the stimulation of sebum formation by testing for the presence of lipid droplets in the absence of the candidate substance and comparing such results to the assay performed in the presence of candidate non-androgen stimulators. The inventor has discovered that the use of TZL in combination with androgen promotes the differentiation of preputial cells to mature sebocytes exhibiting an increase in sebum formation.

In certain embodiments, the present invention concerns a method for identifying such stimulators. It is contemplated that this screening technique will prove useful in the general identification of a compound that will serve the purpose of augmenting or synergizing the effects of androgen in sebocytes, these sebocytes showing an increase in sebum formation. Such compounds will be useful in the treatment of various disorders resulting form the lack of adequate sebum formation, such as eczema, lichenification, iccthyosis and dry skin.

In these embodiments, the present invention is directed to a method for determining the ability of a candidate substance to synergize with androgen in sebum formation, the method including generally the steps of:

(a) providing at least one sebocyte;

(b) contacting said sebocyte with an androgen composition and said candidate substance;

(c) culturing said sebocyte; and (d) assessing sebum formation in said sebocyte.

To identify a candidate substance as being capable of synergizing with androgen, one would measure or determine the activity in the absence of the added candidate substance by adding androgen and monitoring the formation of sebum. One would then add the candidate substance to the cell and determine the levels of sebum formation that arise before and upon addition of androgen in the presence of the candidate substance. A candidate substance which is additive with or synergizes with androgen, and thereby increases the levels of sebum formation relative to the amount of sebum formed in its absence, is indicative of a candidate substance with stimulatory capability.

b. Antagonists of Sebum Formation

These assays may be set up in much the same manner as those described above in assays for non-androgen stimulators. In these embodiments, the present invention is directed to a method for determining the ability of a candidate substance to have an antagonistic effect on sebum formation the method including generally the steps of:

(a) providing at least one sebocyte;

(b) contacting said sebocyte with an androgen composition, a non-androgen stimulator and a candidate inhibitor substance;

(c) culturing said sebocyte; and (d) comparing the formation of sebum in said sebocyte with the formation of sebum in a sebocyte cultured with an androgen composition and an non-androgen stimulator, but in the absence of a candidate inhibitor substance.

As stated above, some non-androgen stimulators may obviate the need for androgen entirely.

To identify a candidate substance as being capable of antagonizing the effect of androgen or a non-androgen stimulator, one would measure or determine such an activity in the absence of the added candidate substance by adding androgen and a stimulator compound and monitoring the formation of sebum. One would then add the candidate antagonist substance to the cell and determine the levels of sebum formation that arise upon addition of androgen and non-androgen stimulator in the presence of the candidate antagonist substance. A candidate substance which is an antagonist decreases the levels of sebum formation, relative to the amount of sebum formed in its.

c. Active Compounds

The active compounds may include fragments or parts of naturally-occurring compounds or may be only found as active combinations of known compounds which are otherwise inactive. Accordingly, the present invention provides screening assays to identify agents which synergize or antagonize with androgen in sebum, it is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds.

The candidate screening assays are quite simple to set up and perform. Thus, in assaying for an non-androgen stimulator after obtaining a sebocyte, one will admix a candidate substance with the cell, under conditions which would allow the formation of sebum but for inclusion of a androgen. In this fashion, one can measure the ability of the candidate substance to stimulate the sebum formation in the absence of the androgen. Likewise, in assays for antagonists after obtaining a sebocyte, one will admix the androgen and a non-androgen stimulator with the cell and determine the sebum formation of the cell. The candidate antagonist substance is then admixed with the cell. In this fashion the ability of the candidate antagonists substance to reduce the formation of sebum may be detected.

"Effective amounts" in certain circumstances are those amounts effective to reproducibly stimulate sebum formation, or to otherwise increase lipid content, in comparison to their normal levels. Compounds that achieve significant appropriate changes in activity will be used.

Significant increase/decrease in sebum formation, e.g., as measured using microscopy or flow cytometry techniques, are represented by an increase in sebum levels of at least about 30%–40%, and most preferably, by increases of at least about 50%, with higher values of course being possible. Assays that measure sebum content are well known to those of skill in the art and include chromatographic and microscopic techniques. The active compounds of the present invention also may be used for the generation of antibodies which may then be used in analytical and preparatory techniques for detecting and quantifying further such inhibitors.

It will, of course, be understood that all the screening methods of the present invention are useful in themselves notwithstanding the fact that effective candidates may not be found. The invention provides methods for screening for such candidates, not solely methods of finding them.

5. Methods of Detection

The present invention encompasses methods for determining the effects of active compounds on the sebum content of sebocytes. Generally, this will be achieved by determining the sebum content of the sebocyte in the presence of the active compounds and comparing the level of the lipids in the sebum with those levels observed in normal cells of the same type. In this manner the amounts of sebum may be quantitated.

Briefly, one will extract the sebum lipid components of a cell by standard methods. Separation of lipid components from (i) non-lipid components and (ii) each other will then permit quantitation of the different lipid species. Quantitation of separated components may be achieved by any standard methodology, but would include photodensitometric scanning of TLC plates, separated by various chromatographic techniques. Alternatively the same techniques could be used with radiolabelled precursors and the quantification of the lipid content could be achieved using scintillation counting of membrane bound or liquid samples.

Any of a wide variety of chromatographic procedures may be employed. For example, thin layer chromatography, gas chromatography, high performance liquid chromatography, paper chromatography, affinity chromatography or supercritical flow chromatography may be employed. See Freifelder, 1982.

Partition chromatography is based on the theory that if two phases are in contact with one another, and if one or both phases constitute a solute, the solute will distribute itself between the two phases. Usually, partition chromatography employs a column which is filled with a sorbent and a solvent. The solution containing the solute is layered on top of the column. The solvent is then passed through the column, continuously, which permits movement of the solute through the column material. The solute can then be collected based on its movement rate. The two most common types of partition chromatograph are paper chromatograph and thin-layer chromatograph (TLC); together these are called adsorption chromatography. In both cases, the matrix contains a bound liquid. Other examples of partition chromatography are gas-liquid and gel chromatography.

Paper chromatography is a variant of partition chromatography that is performed on cellulose columns in the form of a paper sheet. Cellulose contains a large amount of bound water even when extensively dried. Partitioning occurs between the bound water and the developing solvent. Frequently, the solvent used is water. Usually, very small volumes of the solution mixture to be separated is placed at top of the paper and allowed to dry. Capillarity draws the solvent through the paper, dissolves the sample, and moves the components in the direction of flow. Paper chromatograms may be developed for either ascending or descending solvent flow. Two dimensional separations are permitted by changing the axis of migration 90° after the first run.

Thin layer chromatography (TLC) is very commonly used to separate lipids and, therefore, is considered a preferred embodiment of the present invention. TLC has the advantages of paper chromatography, but allows the use of any substance that can be finely divided and formed into a uniform layer. In TLC, the stationary phase is a layer of sorbent spread uniformly over the surface of a glass or plastic plate. The plates are usually made by forming a slurry of sorbent that is poured onto the surface of the gel after creating a well by placing tape at a selected height along the perimeter of the plate. After the sorbent dries, the tape is removed and the plate is treated just as paper in paper chromatography. The sample is applied and the plate is contacted with a solvent. Once the solvent has almost reached the end of the plate, the plate is removed and dried. Spots can then be identified by fluorescence, immunologic identification, counting of radioactivity, or by spraying varying reagents onto the surface to produce a color change.

In Gas-Liquid chromatography (GLC), the mobile phase is a gas and the stationary phase is a liquid adsorbed either to the inner surface of a tube or column or to a solid support. The liquid usually is applied as a solid dissolved in a volatile solvent such as ether. The sample, which may be any sample that can be volatized, is introduced as a liquid with an inert gas, such as helium, argon or nitrogen, and then heated. This gaseous mixture passes through the tubing. The vaporized compounds continually redistribute themselves between the gaseous mobile phase and the liquid stationary phase, according to their partition coefficients.

The advantage of GLC is in the separation of small molecules. Sensitivity and speed are quite good, with speeds that approach 1000 times that of standard liquid chromatography. By using a non-destructive detector, GLC can be used preparatively to purify grams quantities of material. The principal use of GLC has been in the separation of alcohols, esters, fatty acids and amines.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

The gel material for gel chromatography is a three-dimensional network whose structure is usually random. The gels consist of cross-linked polymers that are generally inert, do not bind or react with the material being analyzed, and are uncharged. The space filled within the gel is filled with liquid and this liquid occupies most of the gel volume. Common gels are dextran, agarose and polyacrylamide; they are used for aqueous solution.

High Performance Liquid Chromatography (HPLC) is characterized by a very rapid separation with extraordinary resolution of peaks. This is achieved by the use of very fine particles and high pressure to maintain and adequate flow rate. Separation can be accomplished in a matter of minutes, or a most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography. The generation of antibodies that would be suitable for use in accord with the present invention is discussed below.

6. Methods of Diagnosing Abnormalities in Sebum Formation

It is contemplated that the active compounds of the present invention may be used as diagnostics for abnormalities in sebum formation. As such, the present invention provides diagnostic kits for detecting non-androgen stimulators or antagonists. Such kits will include reagents for determining the presence of the active compounds. These reagents and methods are described below.

a. Immunologic Methods

In one embodiment, the diagnostic approach will be immunologic. The reagents will include antibodies to the non-androgen stimulators and antagonists and will further include reagents capable of detecting an antibody immunoreactive with an such compound. Detection methods include, but are not limited to ELISA, RIA and immunoblots, as discussed elsewhere in the specification.

Antibodies against the antagonists and non-androgen stimulators isolated using the methodology described will be useful in the present invention, primarily in assays for the detection of such antagonists and non-androgen stimulators. In addition, certain antibodies may themselves prove to be antagonistic or synergistic with androgen in the formation of sebum. Means for preparing and characterizing antibodies are well known in the art (see, e.g., Antibodies: A Laboratory Manual, Cold Spring Harbor Laboratory, 1988; incorporated herein by reference).

The methods for generating monoclonal antibodies (MAbs) generally begin along the same lines as those for preparing polyclonal antibodies. Briefly, a polyclonal antibody is prepared by immunizing an animal with an immunogenic composition in accordance with the present invention and collecting antisera from that immunized animal. A wide range of animal species can be used for the production of antisera. Typically the animal used for production of anti-antisera is a rabbit, a mouse, a rat, a hamster, a guinea pig or a goat.

Immunogenic compositions of the invention include non-androgen stimulators such as TZL or fragments and the like, and antagonists isolated by the present invention. As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a compound to a carrier protein are well known in the art and include glutaraldehyde, m-maleimidobenzoyl-N-hydroxysuccinimide ester, carbodiimyde and bis-biazotized benzidine.

As is also well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, also may be given. The process of boosting and titering is repeated until a suitable titer is achieved. When a desired level of immunogenicity is obtained, the immunized animal can be bled and the serum isolated and stored, and/or the animal can be used to generate MAbs.

MAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified protein, polypeptide or peptide. The immunizing composition is administered in a manner effective to stimulate antibody producing cells. Rodents such as mice and rats are preferred animals, however, the use of rabbit, sheep frog cells is also possible. The use of rats may provide certain advantages, but mice are preferred, with the BALB/c mouse being most preferred as this is most routinely used and generally gives a higher percentage of stable fusions.

Following immunization, somatic cells with the potential for producing antibodies, specifically B lymphocytes (B cells), are selected for use in the MAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Campbell, pp. 75–83, 1984). For example, where the immunized animal is a mouse, one may use P3-X63/Ag8, X63-Ag8.653, NS1/1. Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods is also appropriate.

Fusion procedures usually produce viable hybrids at low frequencies, about $1\times10^{-6}$ to $1\times10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid. Radioimmunoassays, enzyme immunoassays, cytotoxicity assays, plaque assays, dot immunobinding assays, and the like, may be used.

Where one desires to generate an antibody with defined activity, one would generally screen the candidate hybridomas to identify those hybridomas that produce antibodies that have the desired inhibitory or stimulatory properties. Any selected hybridomas would then be serially diluted and cloned into individual antibody-producing cell lines, which clones can then be propagated indefinitely to provide MAbs. The cell lines may be exploited for MAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations. MAbs produced by either means may be further purified, if desired, using filtration, centrifugation and various chromatographic methods such as HPLC or affinity chromatography.

Certain aspects of the present invention relates to the detection of non-androgen stimulators and antagonists. One method of detecting such compounds uses immunoassays for agents of the present invention. Antibodies and other toxin binding proteins (i.e., cell surface receptors) that recognize a product or by-product of the active compounds of the present invention are contemplated to be useful in the detection of antagonists and non-androgen stimulators in the immunoassays.

Immunoassays encompassed by the present invention include, but are not limited to those described in U.S. Pat. No. 4,367,110 (double monoclonal antibody sandwich assay) and U.S. Pat. No. 4,452,901 (western blot). Other assays include immunoprecipitation of labeled ligands and immunocytochemistry, both in vitro and in vivo.

Immunoassays, in their most simple and direct sense, are binding assays. Certain preferred immunoassays are the various types of enzyme linked immunosorbent assays (ELISAs) and radioimmunoassays (RIA) known in the art. Immunohistochemical detection using tissue sections is also particularly useful.

In one exemplary ELISA, the antibodies of the invention are immobilized onto a selected surface exhibiting protein affinity, such as a well in a polystyrene microtiter plate. Then, a test composition suspected of containing the desired antigen, such as a clinical sample, is added to the wells. After binding and washing to remove non-specifically bound immune complexes, the bound antigen may be detected. Detection is generally achieved by the addition of another antibody, specific for the desired antigen, that is linked to a detectable label. This type of ELISA is a simple "sandwich ELISA". Detection may also be achieved by the addition of a second antibody specific for the desired antigen, followed by the addition of a third antibody that has binding affinity for the second antibody, with the third antibody being linked to a detectable label.

In another exemplary ELISA, the samples suspected of containing the desired antigen are immobilized onto the well surface and then contacted with the antibodies of the invention. After binding and appropriate washing, the bound immune complexes are detected. Where the initial antigen specific antibodies are linked to a detectable label, the immune complexes may be detected directly. Again, the immune complexes may be detected using a second antibody that has binding affinity for the first antigen specific antibody, with the second antibody being linked to a detectable label.

Competition ELISAs are also possible in which test samples compete for binding with known amounts of labeled antigens or antibodies. The amount of reactive species in the unknown sample is determined by mixing the sample with the known labeled species before or during incubation with coated wells. The presence of reactive species in the sample acts to reduce the amount of labeled species available for binding to the well and thus reduces the ultimate signal.

Irrespective of the format employed, ELISAs have certain features in common, such as coating, incubating or binding, washing to remove non-specifically bound species, and detecting the bound immune complexes. These are described as below.

Antigen or antibodies may also be linked to a solid support, such as in the form of plate, beads, dipstick, membrane or column matrix, and the sample to be analyzed applied to the immobilized antigen or antibody. In coating a plate with either antigen or antibody, one will generally incubate the wells of the plate with a solution of the antigen or antibody, either overnight or for a specified period. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein and solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of the antigen or antibody to the well, coating with a non-reactive material to reduce background, and washing to remove unbound material, the immobilizing surface is contacted with the clinical or biological sample to be tested under conditions effective to allow immune complex (antigen/antibody) formation. Detection of the immune complex then requires a labeled secondary binding ligand or antibody, or a secondary binding ligand or antibody in conjunction with a labeled tertiary antibody or third binding ligand.

"Under conditions effective to allow immune complex (antigen/antibody) formation" means that the conditions preferably include diluting the antigens and antibodies with solutions such as BSA, bovine gamma globulin (BGG) and phosphate buffered saline (PBS)/Tween. These added agents also tend to assist in the reduction of nonspecific background.

The suitable conditions also mean that the incubation is at a temperature and for a period of time sufficient to allow effective binding. Incubation steps are typically from about 1 to 2 to 4 hours, at temperatures preferably on the order of 25° to 27° C., or may be overnight at about 4° C. or so.

Following all incubation steps in an ELISA, the contacted surface is washed so as to remove non-complexed material. Washing often includes washing with a solution of PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact and incubate the first or second immune complex with a urease, glucose oxidase, alkaline phosphatase or hydrogen peroxidase-conjugated antibody for a period of time and under conditions that favor the development of further immune complex formation, e.g., incubation for 2 hours at room temperature in a PBS-containing solution such as PBS-Tween.

After incubation with the labeled antibody, and subsequent to washing to remove unbound material, the amount of label is quantified, e.g., by incubation with a chromogenic substrate such as urea and bromocresol purple or 2,2'-azino-di-(3-ethyl-benzthiazoline-6-sulfonic acid (ABTS) and $H_2O_2$, in the case of peroxidase as the enzyme label. Quantification is then achieved by measuring the degree of color generation, e.g., using a visible spectra spectrophotometer.

Alternatively, the label may be a chemiluminescent one. The use of such labels is described in U.S. Pat. Nos. 5,310,687, 5,238,808 and 5,221,605.

Assays for non-androgen stimulators of the present invention also can determine normal/abnormal tissue distribution for diagnostic purposes. Methods for in vitro and in situ analysis are well known and involve assessing binding of antigen-specific antibodies to tissues, cells or cell extracts. These are conventional techniques well within the grasp of those skilled in the art. For example, the antibodies of the present invention may be used in conjunction with both fresh-frozen and formalin-fixed, paraffin-embedded tissue blocks prepared for study by immunohistochemistry (IHC). Each tissue block may consist of 50 mg of residual "pulverized" prostate tumor. The method of preparing tissue blocks from these particulate specimens has been successfully used in previous IHC studies of various prognostic factors, e.g., in breast cancer, and is well known to those of skill in the art. (Abbondanzo et al., 1990; Allred et al., 1990; Brown et al., 1990)

Briefly, frozen-sections may be prepared by rehydrating 50 ng of frozen pulverized tumor at room temperature in PBS in small plastic capsules; pelleting the particles by centrifugation; resuspending them in a viscous embedding medium (OCT); inverting the capsule and pelleting again by centrifugation; snap-freezing in −70° C. isopentane; cutting the plastic capsule and removing the frozen cylinder fof tissue; securing the tissue cylinder on a cryostat microtome chuck; and cutting 25–50 serial sections containing an average of about 500 remarkably intact tumor cells.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and embedding the block in paraffin; and cutting up to 50 serial permanent sections.

b. Non-Immunologic Methods

Alternatively, one may employ non-immunologic procedures in the diagnostic procedures of the present invention. For example, when examining molecules that are involved in receptor interactions, it is possible to set up assays that look at the occupancy of relevant receptor molecules. This can be performed, for example, by using labeled ligand molecules that will be compete with the ligand (non-androgen stimulators and antagonists) in the sample. The more ligand in the sample, the less labeled receptor that will be bound to the receptor. Such studies can be performed on whole cells as well as on purified receptors. Labels include radiolabels, fluorescent labels and chemilluminscent labels.

Other non-immunologic forms of diagnostic assays include those that look for the presence of functional genes in whole cells derived from the patient. For example, where the non-androgen stimulator or antagonist is a protein, one can look at the corresponding gene to determine if it encodes an active molecule. Examination may simply involve a gross examination of the gene or cDNA for alteration of its size. This permits determination of relatively large deletions or insertions. More subtle analysis, such as looking for RFLP's, will determine both large deletions and a certain class of more subtle mutation, namely, those that affect restriction enzyme sites within the gene. Finally, where a specific genetic lesion has been identified, it is possible to look for that particular change. A popular way to look for these changes is via a template-dependent amplification procedure, such as PCR™.

Rather than looking at a gene per se, one may use a gene from any cell as a "read-out" for the biologic activity of a sample. For example, where certain genes are found to be stimulated or inhibited by the non-androgen stimulators and antagonists of the present invention, it will be possible to look for differential regulation of these genes. This can be accomplished by looking at the mRNA or protein levels of these genes, using standard techniques. In the case of mRNA analysis, it often is desirable, though not necessary, to convert the mRNA to a cDNA. Protein analysis will normally involve the sort of immunologic procedures described above.

7. Pharmaceutical Compositions and Routes of Administration

The present invention provides pharmaceutical compositions for the treatment of disorders in sebum formation. It is contemplated that the antagonists of the present invention will be useful in the treatment of conditions such as acne rosecea and acne vulgaris which manifest as a result of excessive sebum formation. It is further contemplated that non-androgen stimulators will also be useful as pharmaceutical compositions in the treatment of disorders that arise from a lack of sebum formation for example, eczema. Those of skill in the art are well-versed in the diagnosis of conditions appropriate for treatment according to the present invention, and the determination of specific pharmaceuticals, doses and routes of administration for therapies.

Aqueous compositions of the present invention will have an effective amount of an antagonist or an non-androgen stimulator on sebum formation. Such compositions will generally be dissolved or dispersed in a pharmaceutically acceptable carrier or aqueous medium.

The phrases "pharmaceutically or pharmacologically acceptable" refer to molecular entities and compositions that do not produce an adverse, allergic or other untoward reaction when administered to an animal, or human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredients, its use in the therapeutic compositions is contemplated. Supplementary active ingredients, such as analgesics and anti-inflammatory agents, can also be incorporated into the compositions.

In addition to the compounds formulated for parenteral administration, such as those for intravenous or intramuscular injection, other pharmaceutically acceptable forms include, e.g., tablets or other solids for oral administration; time release capsules; and any other form currently used, including cremes, lotions, mouthwashes, inhalants and the like.

The active compounds of the present invention may be formulated for parenteral administration, e.g., formulated for injection via the intravenous, intramuscular, subcutaneous, or even intraperitoneal routes. The preparation of an aqueous composition that contains active compounds of the present invention ingredients will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

The active compounds may be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial ad antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

In certain cases, the therapeutic formulations of the invention could also be prepared in forms suitable for topical administration, such as in cremes and lotions. These forms may be used for treating skin-associated diseases, such as various sarcomas.

Upon formulation, solutions will be administered in a manner compatible with the dosage formulation and in such amount as is therapeutically effective. The formulations are easily administered in a variety of dosage forms, such as the type of injectable solutions described above, with even drug release capsules and the like being employable.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject.

8. Kits

All the essential materials and reagents required for inhibiting or stimulating androgen mediated sebum formation may be assembled together in a kit. When the components of the kit are provided in one or more liquid solutions, the liquid solution preferably is an aqueous solution, with a sterile aqueous solution being particularly preferred.

For in vivo use, an antagonist or stimulator may be formulated into a single or separate pharmaceutically acceptable syringeable composition. In this case, the container means may itself be an inhalant, syringe, pipette, eye dropper, or other such like apparatus, from which the formulation may be applied to an infected area of the body, injected into an animal, or even applied to and mixed with the other components of the kit.

The components of these kits may also be provided in dried or lyophilized forms. When reagents or components are provided as a dried form, reconstitution generally is by the addition of a suitable solvent. It is envisioned that the solvent also may be provided in another container means. The kits of the invention may also include an instruction sheet defining administration of the active compound, or explaining the assays for determining sebum formation in samples.

The kits of the present invention also will typically include a means for containing the vials in close confinement for commercial sale such as, e.g., injection or blow-molded plastic containers into which the desired vials are retained. Irrespective of the number or type of containers, the kits of the invention also may comprise, or be packaged with, an instrument for assisting with the injection/administration or placement of the ultimate complex composition within the body of an animal. Such an instrument may be an inhalant, syringe, pipette, forceps, measured spoon, eye dropper or any such medically approved delivery vehicle. Other instrumentation includes devices that permit the reading or monitoring of reactions in vitro.

9. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Materials and Methods

The present example provides that exemplary protocols used in the present invention. It is of course, understood that the reagents may be substituted by analogous reagent from other sources.

Reagents

Dulbecco's Modified Eagle Medium (DMEM), fetal bovine serum (FBS), penicillin, streptomycin, gentamycin, 0.5% trypsin, phosphate buffered saline without calcium and magnesium (PBS) were obtained from GibcoBRL, Grand island, N.Y. Cellgro Complete (Cellgro), a chemically defined cell culture medium was obtained from Mediatech, Pa. Hydrocortisone was purchased from Steraloids Inc., Wilton, Calif. Bacterial neutral protease II (dispase) was from Boehringer Mannheim, GmbH, Germany. Ethanol was from Midwest Grain Products, Weston, Mo. Cell culture equipment (pipettes, plates, test tubes) and formaldehyde were from Fisher Scientific, Fair Lawn, N.J. Choleratoxin was obtained from ICN, Irvine, Calif. BRL 49653, LY 171883, WY 14643, leukotriene $D_4$ and $B_4$, nordihydroguaiaretic acid, dapsone, MK-571 were from Biomol, Plymouth Meeting, Pa. Cayman Chemical Co., Ann Arbor, Mich. was the source of 15-deoxy-$\Delta^{12,14}$-prostaglandin $J_2$. All remaining reagents and supplies were from Sigma Chemical Co., St. Louis, Mo.

Cell Preparation

Adult male Sprague-Dawley rats, approximately 60 days of age, were obtained from Harlan, Madison, Wis. Handling of rats was in accordance with NIH and UCH guidelines for the care and use of laboratory animals. They were sacrificed by $CO_2$ narcosis and subsequent cervical dislocation. Isolated preputial glands were cleaned from surrounding insulatory tissue, sectioned longitudinally, and placed in a solution of 2.5% dispase in DMEM supplemented with 10% FBS, at 4° C. overnight. Dorsal epidermal skin was dissected from the subdermal adipose tissue and likewise incubated overnight. After the incubation, the skin was incubated at 37° C. for 35 min, and epidermis was removed from the dermis. All tissues were washed in PBS. They were then incubated in 0.5% trypsin, and 0.25% trypsin/0.01% EDTA in PBS, for preputial glands and epidermis, respectively. FBS was added to quench trypsin in 1:1 volume ratio. The preputial cells were then gently scraped off the capsule with a rubber policeman and filtered through a sterile 50 $\mu$m nylon mesh with 10% FBS DMEM. Epidermal cells were vortexed for 5 min and then likewise mesh-filtered. Both cell type suspensions were pelletted at 1000×g.

Riboprobes and RNase Protection Assay

A 275 bp cDNA fragment of rat PPARγ, comprising the 90 bp region specific to PPARγ2 and extending into the A/B domain of cDNA common to both PPARγ1 and γ2, was obtained by reverse transcription coupled to polymerase chain reaction using primers homologous to the mouse PPARγ2 cDNA sequence (Tontonoz et al., 1994). The cDNA strand was synthesized from 5 $\mu$g of total RNA from rat epididymal fat pad using the SUPERSCRIPT II RNase H⁻ Reverse Transcriptase (Gibco BRL, Gaithersburg, Md.). The primers consisted of γ-up 5'-AGTCATGGAACACGGACAGG-3' (SEQ ID NO:1), and γ-down 5'-CTCCATGTTGAGGCTGCCAC-3' (SEQ ID NO:2). The rat cDNA fragment was then sequenced by the dideoxy termination method (Sambrook et al., 1989a) for determination of homologies to mPPARγ. This area of the cDNA allowed the inventors to differentiate between the γ1 and γ2 isoforms using a single riboprobe, as the signal for γ2 is at 275 bp and the signal for γ1 is 90 bp less, or at 185 bp. The 275 bp riboprobe was made by linearizing the plasmid with the restriction enzyme HindIII and then transcribed using T3 RNA polymerase (Sambrook et al., 1989b). For all riboprobe studies, a 109 bp internal control probe was created by linearizing pT7 18S rRNA (Ambion Austin, Tex.) and transcribing with T7 RNA polymerase (Sambrook et al., 1989b).

PPARδ was obtained from Dr. S. Liao (University of Chicago). It consisted of a 1 kb cDNA fragment inserted into the EcoR1 site of the polylinker of pBluescript SK. The 230 bp riboprobe was made by linearizing the plasmid with Msc1 and then transcribing with T7 RNA polymerase as above. It corresponds to base pairs 1166 to 1396 within the ligand binding domain of the cDNA (Xing et al., 1995).

RNase protection assay was performed as previously reported (Miyake et al., 1994). Briefly, total RNA (10 $\mu$g) was hybridized to the riboprobes, unprotected RNA was digested with RNase A and T1, and the protected RNA hybrids were separated on a 5% polyacrylamide/BM urea gel.

Cell Culture

Cells were plated on 35 mm 6-well polystyrene dishes (Costar) containing a feeder layer of J23T3 fibroblasts, supplied by Elaine Fuchs, University of Chicago, which had been pretreated with mitomycin C (8 $\mu$g/mL for 2 hours) and then washed 3 times were PBS (Laurent et al., 1992). 3T3s were plated at a density of 200,000 cells/well (e.g., ≈20,000 cells/cm$^2$) and preputial and epidermal cells were plated at a density of 50,000 cells/well (e.g., ≈5,000 cells/cm$^2$). Cells were grown at 37° C., in 95% air/5% $CO_2$, with 10% FBS DMEM supplemented with 100 mg/mL streptomycin, 100 U/mL penicillin, 0.25 $\mu$g/mL amphotericin B, $5\times10^{-2}$ $\mu$g/mL gentamycin, $10^{-10}$ M cholera toxin, $1.3\times10^{-6}$ M hydrocortisone, and $10^{-6}$ M insulin for 3 days. On day 3, cells were switched to a medium consisting of Cellgro supplemented with the above concentrations of streptomycin, penicillin, amphotericin B, gentamycin, choleratoxin, hydrocortisone, insulin, and various treatments when appropriate. Feedings were performed every other day and the growth studies were stopped after 10 days of culture, e.g., day 9.

Data Collection

Cell cultures were fixed for 10 min with 0.1% formaldehyde in 2% aqueous monohydrous calcium acetate, washed, and stained with 5% Oil Red O in 60% aqueous triethyl phosphate for 10 min (Rosenfield, 1989). Lipid accumulation in cells was quantified by light microscopy at 25–100× in four groups categorized as number of cells per colony: 0 stained cells/colony, 1–5 stained cells/colony, 6–50 stained cells/colony, and >50 stained cells/colony. Cell proliferation was quantified by staining cells with Gill's hematoxylin and categorizing colonies according to 4 criteria: 0–1 mm in diameter, 1–2 mm, 2–3, and 3–4 mm in diameter.

Lipid accumulation was also quantified with differential counts and fluorescence-activated cell scanning (FACScan). Cultured cells were dispersed into single cell suspensions by incubating them with 0.25% trypsin and 0.01% EDTA in PBS for 10 min. For differential counts, cell smears were fixed on poly-L-lysine coated slides, stained with ORO, and counterstained with Gill's hematoxylin; cells were then classified according to their stage of differentiation according to a modification of the method of Tostl (Rosenfield, 1989). For FACScan, dispersed cells were stained for 20 min with 0.1 $\mu$g/ml Nile Red in 0.01% methanol, washed, and resuspended in 1 ml PBS. FACScan excitation wavelength was 488 nm, and emission was monitored through band-pass filters at 585±15 nm (FL2), and ≧630 nm (FL3) (Greenspan et al., 1985; Smyth and Wharton, 1992). The FL1 (525±15 nm) region was gated out after preliminary studies with propidium iodide showed a negligible proportion of nonviable cells. The detector voltage gain settings were calibrated to minimize the autofluorescence signal of unstained cells, and the compensation settings were adjusted to minimize the overlapping Nile Red emission spectrum in the FL2 and FL3 regions. Analysis was performed using Lysis 2.0 software (Becton Dickinson).

Statistical Analysis

One-way analysis of variance followed by an internal comparison of variables using Scheffe's post hoc test to quantify the differences among various treatments. Residual square sum regression models were used to ascertain the degree of synergy between treatments.

Molecular Modeling

Quantitative activity-structure relationship (QSAR) analyses were performed using the APEX-3D module of Insight II 95.0, Biosym/MSI, San Diego, Calif., running on a Silicon Graphics Challenge XL parallel-processing computer.

All biophores were sketched using the Builder module and geometry optimization was carried out using default settings. Conformational isomers of the biophores were generated by 30° rotation about σ bonds and 180° rotation about π bonds; conformers with greater than 10 kcal/mol energy difference from the original, geometry optimized structure, were discarded. Structural indices of the molecules were calculated using the MOPAC 6.0 semi-empirical quantum-chemical program.

EXAMPLE II

Preputial Cells in Culture

Preputial glands were obtained from young adult male Sprague-Dawley rats, about 2 months old and 220 gm weight, which were killed by rapid cervical dislocation. A single cell suspension was then prepared by a modification of the method of Wheatley et al., (1979). Cell clumping was eliminated by the substitution for collagenase of 2.5% dispase (bacterial neutral protease, type II, Boehringer) in Dulbecco's Modified Eagle Medium (DMEM) for 18 h at 4° C. The pellet obtained by centrifugation at 400×g was successively washed with a phosphate buffered saline/1% ethylenediaminoacetic acid (EDTA) and then incubated sequentially with 0.25% trypsin (Gibco) at 37° C. for 40 min and 2.5 mg/ml soybean trypsin inhibitor (Worthington). The cells were then gently stripped from the capsule into DMEM/10% fetal calf serum with a rubber policeman. A cell pellet was prepared after filtering through 52 $\mu$ nylon mesh; it was then taken up into cell culture medium and the cells dispersed by a Pasteur pipette.

Preputial cells develop epithelial colonies similar to those formed by epidermal cells when observed by phase contrast microscopy. However, preputial cells can be identified as a unique epithelial cell population by the naked eye (Laurent et al., 1992): compared to epidermal cells they form a smaller number of larger colonies, grow more slowly, and develop domes before confluence.

Further characterization has shown that cultured preputial cells form very few cornified envelopes relative to epidermal cells (Laurent et al., 1992). In addition, they express a variety of keratins, including a specific cytokeratin of acinar preputial cells, K4, which is found in human sebaceous glands (Latham et al., 1989) but not in epidermis (Moll et al., 1982).

Treatment with β-adrenergic agents causes a more prominent cAMP-dependent protein kinase response in preputial than in epidermal cells in vitro, as in vivo, and brings about a distinctive pattern of protein kinase regulatory subunit predominance (Ellis, 1968). This indicates the presence of adenylate cyclase-coupled β-adrenergic receptors and a specific signal transduction pathway.

All-trans-retinoic acid inhibits proliferation of these sebocytes in vitro by 31% at $10^{-7}$ M and arrests it at $10^{-6}$ M, while having no such effect on epidermal cells (Rosenfield and Deplewski, 1995). These results indicate that the entire signal transduction pathway involved in retinoid action on sebocytes is expressed in cultured preputial cells.

The androgen receptor (AR) content of preputial cells is similar to that of the prostate gland, with 10-fold greater mRNA abundance than in epidermal cells (Miyake et al., 1994). When preputial sebocytes were separated according to their state of differentiation by gradient density centrifugation, sebocytes in the 1.080 density fraction contrasted with the more buoyant fractions in expressing significantly less AR, as determined both by immunocytochemistry and RNase protection assay.

These results suggest that there is little if any AR gene expression in undifferentiated preputial sebocytes (which comprise about 8% of cells in the 1.080 fraction), modest expression of AR in early differentiated sebocytes (which comprise about 40% of the 1.080 fraction), and maximal AR gene expression in mid- to late differentiated sebocytes (which constitute 80% or more of the cells in the more buoyant fractions). In monolayer culture sebaceous epithelial cells express AR mRNA to the same extent as in the 1.080 fraction of freshly dispersed sebocytes, which is about half that of mature sebocytes ($p<0.02$), but about 5-fold greater than that of epidermal cells ($p<0.01$).

EXAMPLE III
Preputial Sebogyte Differentiation is Incomplete in Monolayer Culture Preputial sebocytes do not completely differentiate in monolayer culture. By light microscopy, only occasional preputial cells in culture accumulate the fused lipid droplets that are characteristic of mature sebocytes (Rosenfield, 1989). By electron microscopy it can be seen that preputial cells indeed form abundant tiny lipid droplets, but these droplets fuse in only a very few cells at the center of colonies (Rosenfield, 1989).

This indicates that preputial sebocytes undergo early differentiation in culture, but seldom reach the stage of mid-differentiation at which intracytoplasmic lipid droplets fuse. The level of AR gene expression also indicates that sebocytes do not mature fully in the preputial cell culture system.

Preputial cells were cultured on a 3T3-J2 cell feeder layer in medium containing 10% fetal calf serum (FCS) and supplemented with insulin (10-6 M), cortisol (10-6 M) and choleratoxin (10-10M), as previously reported (Rosenfield, 1989). The colonies were treated in triplicate from day 3 to 9 with or without DHT (10-6 M) and/or BRL (10-6 M). Terminally differentiating or lipid forming colonies (LFCs) were defined as those containing over 5 sebocytes with fused lipid droplets according to Oil Red O (ORO) staining (Rosenfield, 1989) on day 9. Only 5±4% (mean±SD, n=3) of preputial sebocyte colonies cultured with or without DHT contained LFCs. However, clusters of differentiating sebocytes could be seen for the first time with BRL treatment, particularly in the presence of DHT (FIG. 4).

Subsequently it was found that sebocyte differentiation was better, although growth was about one-third less ($p<0.05$), if a serum-free, chemically defined medium was substituted from day 3 of culture onward. Using this system, 5 experiments showed the following percentages of preputial cell colonies to differentiate into LFCs: Control 11±6%, DHT 25±9%, BRL 66±12%, and DHT plus BRL 80±6%. The differences among these treatments were all significant ($p<0.01$) according to one way analysis of variance followed by Scheffe's post-hoc test.

The hypolipemic fibrate WY-14643 (WY) $10^{-6}$ M and linoleic acid (LIN) $10^{-4}$ M as these are respectively particularly informative about PPARα (Lehmann et al., 1995; Forman et al., 1995, Braissant et al., 1996) and PPARδ (Lehmann et al., 1995) (also termed PPARβ, NUC-1, and FAAR (Schoonjans et al., 1996; Braissant et al., 1996). WY induced 20%±4.2% and LIN over 95% LFCs; no interaction with DHT was found. RNase protection assay (Miyake K et al., 1994) showed abundant gene expression of the PPARγ1 isoform in sebocytes from fresh tissue, and less in cultured sebocytes (FIG. 11).

These studies demonstrate that androgens have a small but distinct effect on sebocyte differentiation which is additive with that of PPAR activation. Furthermore, PPAR activation is necessary for the lipogenesis that characterizes the late stages of sebocyte differentiation.

PPARα and PPARδ, but not PPARγ, have been detected in rat sebaceous glands by in situ hybridization (Brun et al., 1996). We used a more sensitive technique, RNase protection assay, to determine if PPARg is present in rat preputial sebocytes. This indeed proved to be the case. The data show abundant gene expression of PPARγ in sebocytes from fresh tissue, but less in cultured sebocytes. Taken together, these data suggest that PPARγ is induced during sebocyte differentiation and represents a possible control point in lipogenesis, whereas gene expression of other PPARs is constitutive.

Activation of any of the PPARs seems capable of inducing sebocyte lipogenesis. The combination of the high potency of the PPARδ activator LIN and the constitutively high expression of PPARδ suggest that PPARδ plays a role in sebocyte terminal differentiation, which is in contrast to fat cells in which activation of PPARδ is ineffective (Brun et al., 1996). The concentration of LIN which results in complete sebocyte differentiation, 0.1 mM, is a physiologic fatty acid level in sebum (Wheatley, 1986).

Androgen has a paradoxical effect in this system (Rosenfield et al., 1993). Androgen inhibits preputial sebocyte proliferation via an AR-dependent mechanism: DHT $10^{-7}$ M inhibited proliferation of sebocytes (63.8±6.8, SEM, % of control; $p<0.005$), but not of epidermal cells, and the antiandrogen hydroxyflutamide competitively blocked the DHT effect. Furthermore, hydroxyflutamide alone stimulated sebocyte growth, apparently by blocking the action of the nanomolar amount of androgens present in fetal calf serum.

These results show that androgen acts to switch early differentiated preputial sebocytes from a proliferative mode to a more differentiated mode, but the latter cannot be expressed because an inhibitory influence upon lipogenesis is imposed by the tissue culture system. Whether DHT exerts its effect on the sebocyte or the feeder layer is unknown.

A certain sequence in the development of hormonal responsiveness during sebocyte differentiation may be deduced from these studies (Table 1): 1) full responsiveness to retinoic acid occurs early in sebocyte differentiation, 2) the βadrenergic and androgen signal transduction pathways seem to be in place within this stage of differentiation, but 3) full responsiveness of sebocyte lipogenesis to androgen and catechols does not become possible until later in differentiation.

In conclusion, these results imply that androgen acts, in some as yet poorly understood manner, to increase downstream PPAR expression, which in turn transduces the terminal differentiation of sebocytes. These results have implications for the development of new treatments for acne.

TABLE 1

Proposed Model of Structure-Function
Relationships in Sebocyte Development

| Sebocyte stage | Lipid formation | Hormonal responsiveness |
|---|---|---|
| Undifferentiated | None | None |
| Early differentiated | Perinuclear droplets | Retinoid responsiveness<br>β-adrenergic signal transduction<br>Androgen signal transduction |
| Mid-differentiated | Fused droplets | Enhancement of lipogenesis |
| Late differentiated | Drops | Induction of endonuclease? |

EXAMPLE IV

The Challenge of Attaining Complete Sebocyte Differentiation in Culture

In order to study preputial sebocyte development in the absence of a feeder layer, the present study uses conditionally immortal mouse preputial cells. Preputial cells have been grown from a transgenic mouse homozygous for a temperature sensitive strain of the simian virus large tumor antigen which is linked to an interferon-inducable promoter (Jat et al., 1991). These cells attach and grow well without a feeder layer in the presence of 10% FCS, choleratoxin, cortisol and γ-interferon. Data form this study show that sebocytes from this culture system are capable of differentiating further than wild type preputial cells: they develop more fused lipid droplets than epidermal cells similarly prepared, according to Nile Red fluorescence.

Although sebaceous gland development is androgen-dependent, androgens like dihydrotestosterone (DHT) induce sebocytes to differentiate only incompletely in monolayer culture, that is, cultured sebocytes form few of the fused lipid droplets which are characteristic of mature sebocytes. The inventors have discovered that the factor required for complete differentiation is a peroxisome proliferator. In support of this theory, the effect of BRL-49653, a thiazolidinedione, on sebocyte differentiation was tested.

Rat preputial sebocytes were plated on monolayer culture in the presence of a $J_2$, 3T3 cell feeder layer, cortisol ($10^{-6}$ M), choleratoxin ($10^{-6}$ M), and insulin ($10^{-6}$ M) in 10% fetal calf serum. DHT ($10^{-6}$ M) and/or BRL ($10^{-10}$ M to $10^{-6}$ M) were added in serum free medium (Cellgro) from days 3 to 9 of culture, after which the colonies were stained with Oil Red O. Means of 3 experiments performed in triplicate are reported.

The data are reported in Tables 2–9. DHT (Table 3) under these conditions induced appreciable sebocyte differentiation (here defined as >5 sebocytes with fused lipid droplets in a colony) in only 24% of colonies: control 11%. BRL alone exerted a dose-dependent effect (Table 4, Table 5 and Table 6), with 65% of colonies achieving this milestone at a does of $10^{-6}$ M (Table 6). The effects of androgen and BRL appear to be additive (Table 7, Table 8, and Table 9). Synergism may be present in the induction of highly differentiated colonies (>50 fat-positive cells per colony; Table 1, Table 6, and Table 9).

TABLE 2

Sebum formation in Control cells with no androgen or BRL added

| Variable | Obs | Mean | Std. Dev. | Min | Max |
|---|---|---|---|---|---|
| no sebum 0 fat ⊕ cells | 14 | 81.96429 | 9.498712 | 68.3 | 95.6 |
| % colonies with 1–5 fat ⊕ cells | 14 | 6.028571 | 3.4562854 | 1.1 | 12.7 |
| % colonies with 6–50 fat ⊕ cells | 14 | 10.58571 | 7.430276 | 2.2 | 24.3 |
| % colonies with >50 fat ⊕ cells | 14 | .7407143 | 1.091305 | −.03 | 3.1 |
| sum of 6–50 and >50 fat ⊕ cells | 14 | 11.32643 | 8.023061 | 2.2 | 27.2 |

TABLE 3

Sebum formation in Cells with $10^{-6}$M DHT added

| Variable | Obs | Mean | Std. Dev. | Min | Max |
|---|---|---|---|---|---|
| no sebum 0 fat ⊕ cells | 15 | 70.63333 | 11.12248 | 54.7 | 85.9 |
| % colonies with 1–5 fat ⊕ cells | 15 | 4.806667 | 2.131219 | 2 | 8.7 |
| % colonies with 6–50 fat ⊕ cells | 15 | 23.09333 | 9.511006 | 10.4 | 35.8 |
| % colonies with >50 fat ⊕ cells | 15 | 1.672667 | 2.349661 | −2.86e-08 | 8 |
| sum of 6–50 and >50 fat ⊕ cells | 15 | 24.766 | 10.45031 | 11.17 | 37 |

TABLE 4

Sebum formation in Cells with $10^{-10}$M BRL added

| Variable | Obs | Mean | Std. Dev. | Min | Max |
|---|---|---|---|---|---|
| no sebum 0 fat ⊕ cells | 15 | 68.95557 | 13.15054 | 43.8 | 86.9 |
| % colonies with 1–5 fat ⊕ cells | 15 | 4.46 | 1.688956 | 1.9 | 7.8 |
| % colonies with 6–50 fat ⊕ cells | 15 | 20.73333 | 7.172633 | 10.6 | 33 |
| % colonies with >50 fat ⊕ cells | 15 | 5.918 | 9.729285 | −2.86e-08 | 33.9 |
| sum of 6–50 and >50 fat ⊕ cells | 15 | 26.65133 | 13.58587 | 10.6 | 53.5 |

TABLE 5

Sebum formation in Cells with $10^{-8}$M BRL added

| Variable | Obs | Mean | Std. Dev. | Min | Max |
|---|---|---|---|---|---|
| no sebum 0 fat ⊕ cells | 15 | 53.51333 | 7.225339 | 39.8 | 67.2 |
| % colonies with 1–5 fat ⊕ cells | 15 | 5.297333 | 4.028696 | .9 | 13.5 |
| % colonies with 6–50 fat ⊕ cells | 15 | 30.74667 | 6.459308 | 19.4 | 42.3 |
| % colonies with >50 fat ⊕ cells | 15 | 10.494 | 6.835256 | 3.6 | 32.7 |
| sum of 6–50 and >50 fat ⊕ cells | 15 | 41.24067 | 7.963451 | 25.3 | 56.6 |

TABLE 6

Sebum formation in Cells with $10^{-6}$M BRL added

| Variable | Obs | Mean | Std. Dev. | Min | Max |
|---|---|---|---|---|---|
| no sebum 0 fat ⊕ cells | 15 | 29.33333 | 14.17703 | 8.800003 | 53.3 |
| % colonies with 1–5 fat ⊕ cells | 15 | 5.826667 | 3.096188 | 2.3 | 13.9 |
| % colonies with 6–50 fat ⊕ cells | 15 | 36.1 | 10.80833 | 10.5 | 53.7 |
| % colonies with >50 fat ⊕ cells | 15 | 29.694 | 12.36886 | 6.8 | 47.8 |
| sum of 6–50 and >50 fat ⊕ cells | 15 | 65.794 | 14.92335 | 38.9 | 88.3 |

TABLE 7

Sebum formation in Cells with DHT + BRL$^{-10}$M added

| Variable | Obs | Mean | Std. Dev. | Min | Max |
|---|---|---|---|---|---|
| no sebum 0 fat ⊕ cells | 15 | 64.22 | 9.177784 | 40.8 | 78.8 |
| % colonies with 1–5 fat ⊕ cells | 15 | 5.746667 | 4.199467 | 4.77e-08 | 14 |
| % colonies with 6–50 fat ⊕ cells | 15 | 27.56667 | 9.317086 | 15.9 | 51.3 |
| % colonies with >50 fat ⊕ cells | 15 | 2.706 | 1.818291 | 0 | 6.4 |
| sum of 6–50 and >50 fat ⊕ cells | 15 | 30.27267 | 10.50373 | 18.7 | 55.2 |

TABLE 8

Sebum formation in Cells with DHT + BRL$^{-8}$M added

| Variable | Obs | Mean | Std. Dev. | Min | Max |
|---|---|---|---|---|---|
| no sebum 1–5 fat ⊕ cells | 15 | 32.88 | 9.142381 | 22.9 | 51.1 |
| % colonies with 1–5 fat ⊕ cells | 15 | 5.4 | 1.352247 | 3.8 | 8.2 |
| % colonies with 6–50 fat ⊕ cells | 15 | 44.13333 | 10.57907 | 28.6 | 63.3 |
| % colonies with >50 fat ⊕ cells | 15 | 17.694 | 10.02238 | 4.97 | 33.6 |
| sum of 6–50 and >50 fat ⊕ cells | 15 | 61.82733 | 8.66494 | 44.67 | 71 |

TABLE 9

Sebum formation in Cells with DHT + BRL$^{-6}$M added

| Variable | Obs | Mean | Std. Dev. | Min | Max |
|---|---|---|---|---|---|
| no sebum 0 fat ⊕ cells | 15 | 15.20667 | 6.59182 | 6.299997 | 29.8 |
| % colonies with 1–5 fat ⊕ cells | 15 | 4.8 | 3.966647 | 9.54e-08 | 13.5 |
| % colonies with 6–50 fat ⊕ cells | 15 | 26.16 | 8.05373 | 12.6 | 37.9 |
| % colonies with >50 fat ⊕ cells | 15 | 53.694 | 12.78411 | 34.67 | 75.9 |
| sum of 6–50 and >50 fat ⊕ cells | 15 | 79.854 | 6.990559 | 64.67 | 89.39999 |

Figure 2:
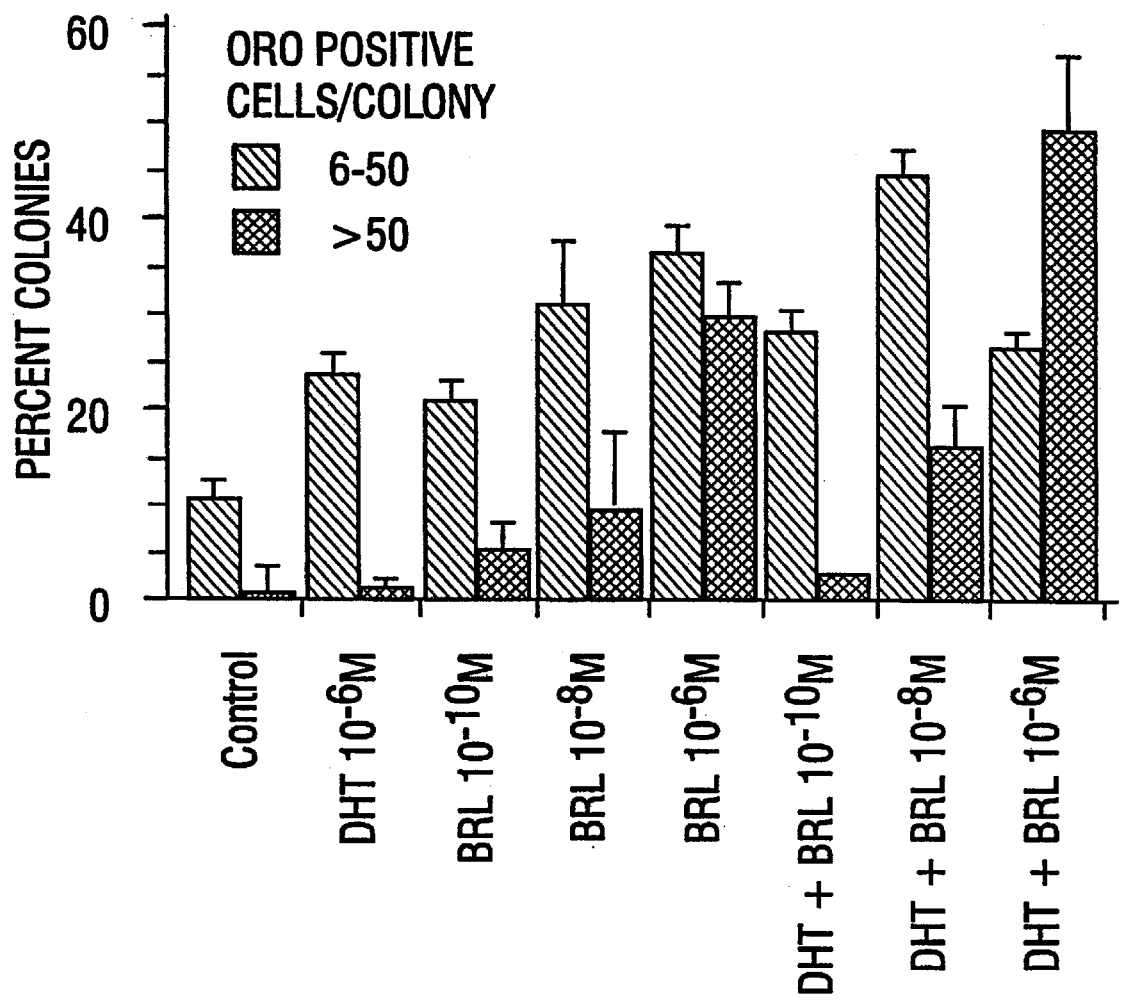

These data are further presented in FIG. 2, it is seen that DHT alone induces an intermediate degree of sebocyte differentiation (6-50 ORO-positive cells/colony), but not highly differentiated colonies (>50 ORO-positive cells/ colony). BRL-49653 alone at the lowest dose was similar to DHT in its effect, but has a marked, dose-related effect on the degree of sebocyte differentiation. DHT markedly interacts with high-dose BRL-49653 to induce highly differentiated sebocyte colonies. None of these treatments affects colony number or size. Data are mean±SEM.

Lipid determination by flow cytometry showed significant differences between control (100±0%) & DHT (135±7%) and BRL-49653 (702±27%) & DHT+BRL-49653 (938±34%). Although this method is not as sensitive for the detection of the DHT effect, these results provide an independent confirmation of the semiqualitative method used above.

Figure 5:
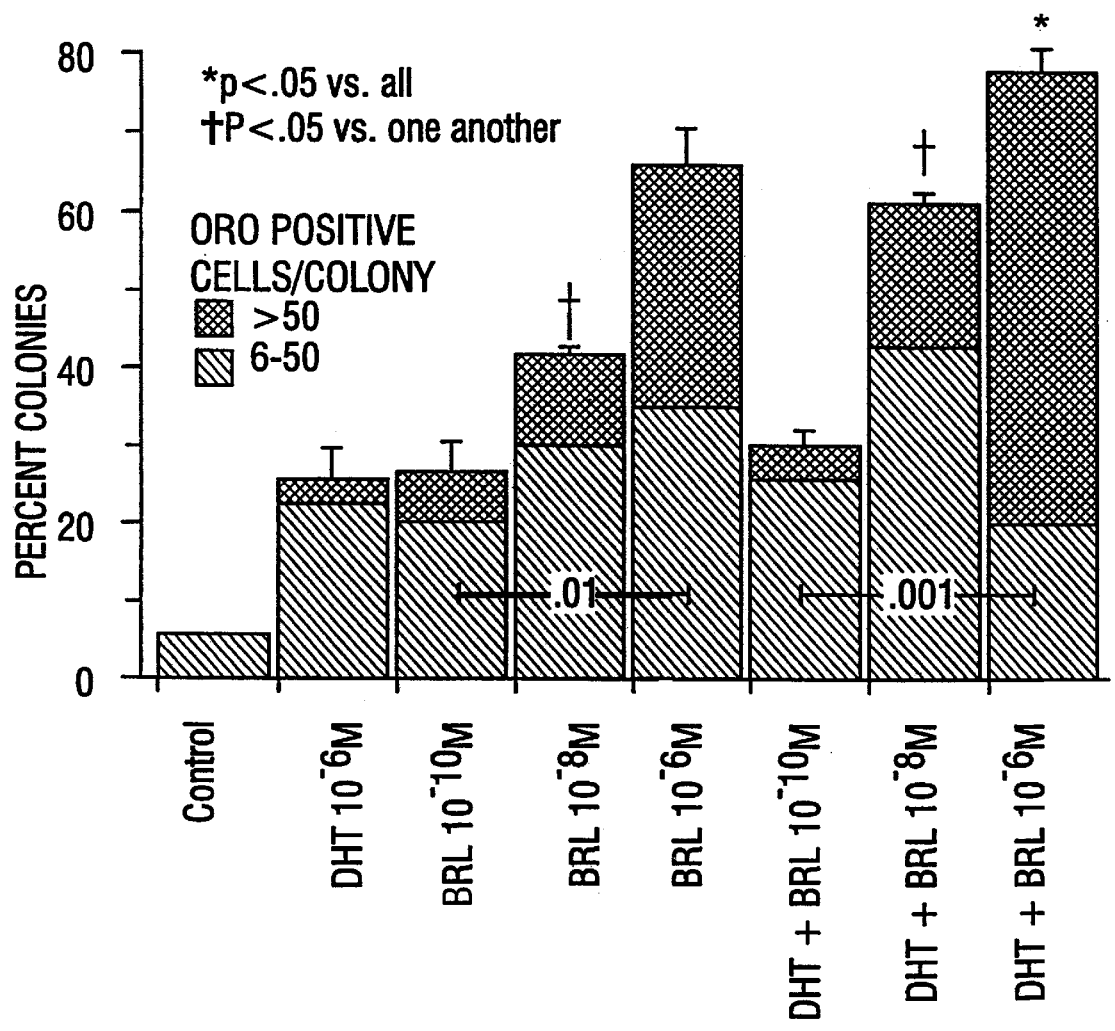

BRL induced prominent sebocyte differentiation, as measured by induction of lipid-forming colonies (LFCs) in a broad, dose-response manner commencing at $10^{-10}$ M in serum-free medium (FIG. 5). Preliminary studies yielded intermediate effects at intermediate BRL doses, with BRL $10^{-6}$ M yielding a maximum response and BRL $10^{-4}$ M having a cytotoxic effect. In 26 studies to date, BRL $10^{-8}$ M induced 80.4±3.8% (SEM) of colonies to differentiate as LFCs, as compared with 5.2±0.7% of untreated controls Although an androgen effect cannot be demonstrated in the presence of fatal calf serum (FCS) in culture medium, a small but significant effect of DHT $10^{-6}$ M on sebocyte differentiation was observed in serum-free, chemically defined medium. DHT $10^{-6}$ M was similar in effect to BRL $10^{-1}$M. Larger DHT doses or administration of the more potent, nonmetabolizable androgen mibolerone led to no greater effect. DHT $10^{-8}$ M enhanced the effect of BRL (FIG. 5). In 26 studies to date, DHT caused 14.8±1.3% of colonies to develop as LFCs p<0.01 vs controls) and DHT plus BRL (each 1 $\mu$M) brought about 70.3±3,1% LFCs (p<0.001 vs BRL alone). There was, however, a suggestion of synergism in the number of colonies that were highly differentiated: the percent of highly differentiated colonies (those containing over 50 lipid-positive cells per colony) was 1.7±0.5% with DHT alone, 30±3.2% with BRL alone, and 54±3.3% with DHT+BRL.

The stimulation of lipid formation by DHT and BRL was also quantified by fluorescence-activated cell scanning, evaluating Nile Red fluorescence for the yellow-gold spectrum characteristic of neutral lipids. FIG. 6 shows the results of one of five studies. Relative to controls, DHT brought about a 1.4±0.1 fold increase in neutral fats (p<0.05); BRL caused a 7.0±0.3 fold increase and DHT plus BRL a 9.4±0.3-fold increase (p<0.001 vs all others).

These results show an important role for PPARs in sebocyte maturation and have implications for the development of new therapeutic modalities for acne.

EXAMPLE V

Use of Peroxisome Proliferators Other Than BRL in Sebum Formation

If the thiazolidinedione BRL induces sebocyte differentiation via a PPAR-mediated pathway, one might expect other PPAR activators to be effective. This example shows data from further studies on sebum formation conducted using inhibitors other than BRL-49653 to synergize with androgen in sebum formation. Two peroxisome proliferators structurally unrelated to BRL-49653, WY-14643 and LY-171883, a hypolipemic agent and a leukotriene D4 receptor antagonist, respectively, were used to stimulate sebum production. Both preferentially stimulate PPARα over PPARγ. Indomethacin also was tested. It paradoxically stimulated sebum formation. This suggested that alternative arachidonic acid metabolites might activate other PPAR's, e.g., leukotrienes.

Figure 3:
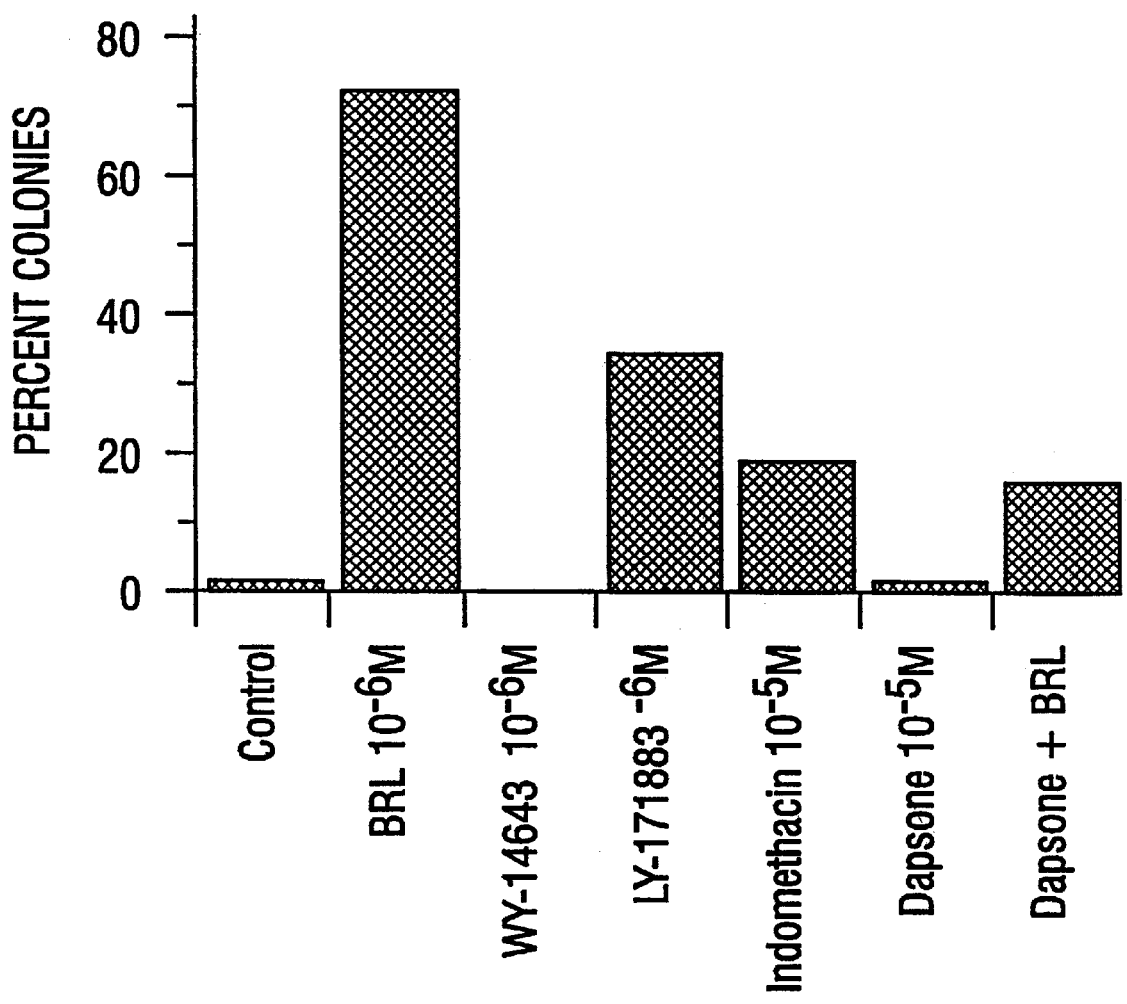
Figure 4A:
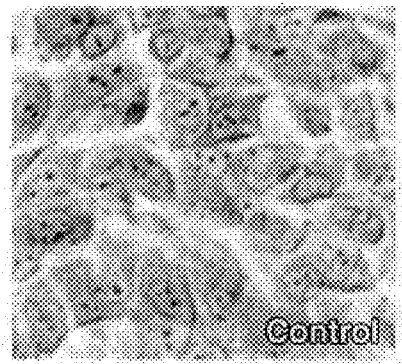
FIG. 4A, FIG. 4B, FIG. 4C and FIG. 4D. Differentiation of preputial sebocytes in a primary epithelial cell culture system containing 10% fetal calf serum, as assessed by Oil Red O staining. Treatments consisted of control (FIG. 4A), DHT 10-6 M (FIG. 4B), the thiazolidinedione BRL-49653 (BRL) 10-6 M (FIG. 4C), or DHT plus BRL (FIG. 4D). The most prominent sebocyte differentiation occurred in the presence of DHT plus BRL.
Figure 4B:
Figure 4C:
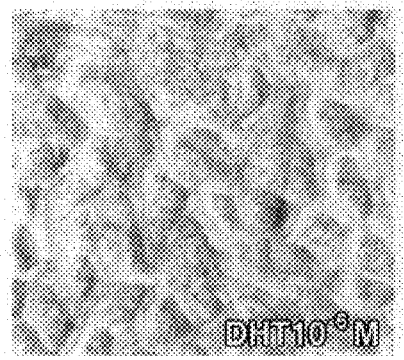
Figure 4D:
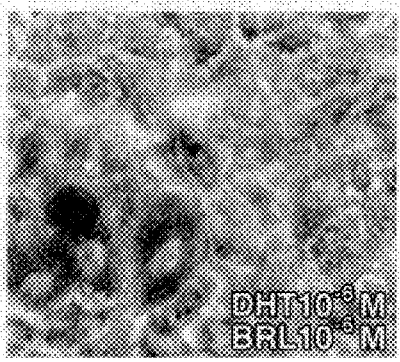

WY $10^{-6}$ M stimulated 19.8±5.1% LFCs, and WY $10^{-5}$ M stimulated significantly more (83±1.1%) (FIG. 3). The inventors also tested a maximally tolerated dose of LY-171883 (LY), a non-thiazolidinedione which activates PPARγ preferentially to PPARα (Lehmann et al., 1995). FIG. 3 shows that $10^{-6}$ M LY stimulated lipogenesis (28.3±1.3% LFCs, p<0.01 vs control). Neither BRL nor DHT had an additive effect with WY or LY.

Data presented in FIG. 3 show that percent of colonies with moderate or greater differentiation (>5 ORO-positive cells/colony). BRL-49653 has the expected effect versus control. WY-14643 at 10 μM was a potent stimulator of lipogenesis—WY-14643 causes 82% of cells to differentiate to the moderate or greater degree (three experiments). LY-171883 at 30 μm is completely antiproliferative. The effectiveness of three activators of peroxisome proliferation that act by diverse mechanisms points strongly to PPAR's as key factors in sebum formation.

Indomethacin has the effect of moderately stimulating lipogenesis. This suggests that the alternate lipooxygenase pathway of prostaglandin metabolism to leukotrienes is involved in sebocyte differentiation. Dapsone which is a leukotriene B4 antagonist was tested with BRL-49653. These results suggest that it dapsone and hence inhibition of leukotriene B4 may inhibit the sebocyte differentiation induced by BRL. This points to a previously unsuspected class of substances that have the potential to reduce sebum formation and acne.

LIN, an instructive PPARδ activator, was then tested. LIN $10^{-4}$ M induced over 95% of LFCs (n=9). LIN yielded a steep dose-response effect on sebocyte maturation with a marginal effect at $10^{-5}$ M and a maximal response at $10^{-4}$ M. Over 80% of individual preputial cells differentiated in response to LIN $10^{-4}$ M, several-fold more than in response to any other PPAR activator, including the combination of BRL and WY (p<0.001) (FIG. 8). Fully mature cells averaged 25.5%±5.2% of the total on LIN $10^{-4}$ M. No interaction with DHT, BRL or WY was seen. LIN caused diffuse differentiation of cells throughout colonies, whereas BRL and WY caused differentiation only in the central zone of colonies where the older cells reside (FIG. 9A through FIG. 9F).

EXAMPLE VI
PPAR Activation Specificity For Sebaceous Epithelium

Lipid droplet formation could not be discerned in cultured skin epidermal cells after incubation with BRL, WY, or LY in doses effective in inducing sebocytes to form LFCs. LIN, however, was as effective at inducing LFCs in epidermal cell as in sebocyte colonies (FIG. 10C). LIN also induced lipid droplet formation fn the 3T3-J2 cells of the feeder layer (FIG. 9F).

EXAMPLE VII
Molecular Basis of PPAR Activator Action

Since the activation of sebocyte lipogenesis by a thiazolidinedione and LIN suggested a prime role of PPARγ and PPARδ, the inventors have sought their expression in sebocytes by RNase protection essay (RPA). A 275 bp cDNA fragment for rat PPARγ1 and γ2 was obtained using primers homologous to the A/B domain of mouse PPARγ (Tontonoz et al., 1994). A 230 bp cDNA fragment within the ligand binding domain of rPPARδ was used for riboprobe synthesis. Homologies of rat (SEQ ID NO:4) to mouse (SEQ ID NO:3) PPARγ were shown in FIG. 10. The inventors then prepared rat PPAR riboprobes and demonstrated PPARγ and PPARδ in freshly dispersed sebocytes (FIG. 11). This is the first demonstration of PPARγ mRNA expression in a sebaceous gland and shows the γ1 isoform, but not the γ2 isoform found in fat. PPARγ1 is detectable in cultured sebocytes at a lower level of abundance. RPA also showed that PPARδ is expressed in both freshly dispersed and cultured sebocytes and is more prominent in cultured sebocytes than is PPARγ (FIG. 11).

EXAMPLE VIII
Growth Hormone (GH) and DHT Interact to Stimulate Sebaceous Cell Differentiation Acne vulgaris, a sebaceous gland disorder, does not occur until androgen levels begin to rise at puberty. However, GH and IGF-1 levels parallel the course of acne more closely than androgen levels in that they peak in mid-adolescence and then subside at 18 years of age, while androgen levels plateau. The inventors tested the possibility that GH interacts with androgen to stimulate sebocyte formation.

Rat preputial sebocytes were grown in monolayer culture on a mitomycin C-treated cell feeder layer as described above. Treatments with recombinant human GH ($10^{-10}$–$10^{-6}$M), with or without DHT ($10^{-6}$M) were performed in triplicate in serum free medium from days 3 to 9. Cell proliferation was determined by $^3$H-thymidine incorporation (n=5), and cell differentiation was determined by Oil Red O staining with lipid forming colonies (LFC) being defined as those colonies with greater than 5 cell positive for lipid droplets (n=3).

GH did not change sebocyte proliferation at any doses tested. DHT however, decreased cell proliferation by 40% (p<0.05 vs. control), an effect unaltered by GH.

GH increased cell differentiation in a dose related manner: GH $10^{-10}$M, $10^{-8}$M and $10^{-6}$M caused 27%, 41% and 42% LFC respectively (p<0.05 for $10^{31\ 10}$M vs. all others). DHT alone stimulated LFC (32%). The addition of GH at concentration greater than or equal to $10^{-8}$M to DHT increased LFC to 49% (p<0.05 vs. DHT) and GH $10^{-10}$M plus DHT caused more LFC than GH alone (p<0.05). Studies suggest that sebocytes do not grow or differentiate in the absence of insulin and differentiation may be restored by a dose of GH ($10^{-8}$M) that is insufficient to restore growth.

These data suggest that GH directly stimulates sebaceous cell differentiation in vitro and that this effect is additive with that of DHT. These data also imply that GH generates local IGFs that may substitute for insulin in sebocyte differentiation. Furthermore these data support the theory that the increase in GH production at puberty contributes to the flare in acne in adolescence.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Abbondanzo et al, *Breast Cancer Res. Treat.*, 16:182(#151), 1990.
Akamatsu H, Zouboulis C, Ofanos C E, *J Invest Dermatol*, 99:509–511, 1992.
Akamatsu H, Zouboulis C, Orfanos C E, *J Invest Dermatol*, 100:660–662, 1993.
Allred et al., *Breast Cancer Res. Treat.*, 16:182(#149), 1990.
Alves et al., *J Endocr.*, 109:1–7, 1986.
Amri, Bonino, Ailhaud, Abumrad, Grimaldi, *J Biol. Chem.*, 270:2367–2371, 1995.
Antibodies: A Laboratory Manual, Cold Spring Harbour Laboratory, 1988.
Apfel, Bauer, Crettaz, Forni, Kamber, Kaufmann, LeMotte, Klaus, *Proc. Natl. Acad. Sci. USA*, 89:7129–7133, 1992.
Boris A, Hurley J, Wong C Q, Comai K, Shapiro S, *Arch Dermatol Res*, 280:246–251, 1988.
Brandes, Hertz, Arad, Naishat, Weil, Bar-Tana, *Life Sci.*, 40:935–941, 1977.
Brind et al., *J Endocr.*, 100:377–388, 1984.
Brown and Williams, "The rodent preputial gland," *Mammal Review*, 2:105–147, 1972.
Brown et al., *Breast Cancer Res. Treat.*, 16:192(#191), 1990.
Chawla and Lazar, *Proc. Natl. Acad Sci. USA*, 91:1786–1790, 1994.
Chawla, Schwarz, Dimaculangan, Lazar, *Endocrinology*, 135:798–800, 1994.
Chen, Law, O'Malley, *Biochem. Biophys. Res. Comm.*, 196:671–677, 1993.
Dreyer, Krey, Keller, Givel, Helftenbein, Wahli, *Cell*, 68:879–887, 1992.
Ebling F J, *Acta Endocrinol*, 72:361–365, 1973.
Ellis R A, In: *Biopathology of pattern alopecia*, Baccaredda-Boy, Morretti G, Frey J R (eds). Karger, Basel, 146–154, 1968.
Evans, *Science*, 240:889–895, 1988.
Forman, et al., "15-deoxy-$\Delta^{12,14}$-prostaglandin $J_2$ is a ligand for the adipocyte determination factor PPAR$\gamma$," *Cell*, 83:803, 1995.
Freifelder, *Physical Biochemistry*—2d Ed., W. H. Freeman & Co., 1982.
Fukishima, M., *Essent. Fatty Acids*, 47:1–12, 1992.
Gefter et al. *Somatic Cell Genet*. 3:231–236 (1977).
Giles and Leff, 1988 "The biology and pharmacology of Pgd2" Prostaglandins, 35: 277–299.
Goldman A S, Katsumata M, Goto M P, "Lipokinins: Novel phospholipase $A_2$ activators mediate testosterone effects on embryonic genitalia," *J Urol*, 140:1184, 1988.
Gomez E C, Martinez C A, *J Am Acad Dermatol*, 6:746–750, 1982.
Green and Chambon, *Trends Genet.*, 4:309–315, 1988.
Heyman, Mangelsdorf, Dyck, Stein, Eichele, Evans, Thaller, *Cell*, 68:397–406, 1992.
Issemann and Green, *Nature*, 347:645–650, 1990.
Jat P S, Noble M D, Ataliotis P, Tanaka Y, Yannoutsos N, Larsen L, Kiousis D, *Proc Natl Acad Sci (USA)*, 88:5096–5100, 1991.
Jenkinson D M, Elder H Y, Montgomery I, Moss VA, *Tissue and Cell*, 17:683–698, 1985
Kliewer S A, Lenhard J M, Willson T M, et al., "A prostaglandin $J_2$ metabolite binds peroxisome proliferator-activated receptor and promotes adipocyte differentiation," *Cell*, 83:813, 1995.
Kliewer, Forman, Blumberg, Ong, Borgmeyer, Mangelsdorf, Umesono, Evans, *Proc. Natl. Acad. Sci. USA*, 91:7355–7359, 1994.
Kohler & Milstein, *Eur. J Immunol.*, 6:511–519, 1976.
Kohler & Milstein, *Nature*, 256:495–497, 1975.
Latham J A E, Redfem C P F, Thody A J, de Kretser T A, *J Histochem Cytochem*, 37:729–734, 1989.
Laurent S J, Mednieks M I, Rosenfield R L, *In Vitro Cell Dev Biol*, 28A:83–89, 1992.
Lehmann, John, Fanjul, Camerson, Lu, Haefner, Dawson, Pfahl, *Science*, 258:1944–1946, 1992.
Levin, Sturzenbecker, Kazmer, Bosakowski, Huselton, Allenby, Speck, Kratzeisen, Rosenberger, Lovey, Grippo, *Nature*, 355:359–361, 1992.
Luu-The V, Sugimoto Y, Puy L, Labrie Y, Solache I M, Singh M, Labrie F, *J Invest Dermatol*, 102:221–226, 1994.
Mangelsdorf, Ong, Dyck, Evans, *Nature*, 345:224–229, 1990.
Mednieks M I, Laurent S J, Hand A R, Rosenfield R L, *J Invest Dermatol*, 97:517–523, 1991.
Mesquita-Guimaraes, Coimbra A, *Arch Dermatol Res*, 270:325–331, 1981.
Miyake K, Ciletti N, Liao S, Rosenfield R L, *J Invest Dermatol*, 103:721–725, 1994.
Moll R, Franke W W, Shiller D L, Geiger B, Krepler R, *Cell*, 31:11–24, 1982.
O'Malley and Conneely, *Mol. Endocrinol.*, 6:1359–1361, 1992.
Plewig et al., *Acta Dermatovener*, 51:413–422, 1971.
Rosenfield R L, *Clin Endocrinol Metab*, 15:341–362, 1986.
Rosenfield R L, Deplewski D, *Am J Med*, 98 (suppl 1A):80S–88S, 1995.
Rosenfield R L, *J Invest Dermatol*, 92:751–754, 1989.
Rosenfield R L, Miyake K, Ciletti N, Liao S, *Clin Res*, 41:257A, 1993.
Rosenfield, Robert L., "Relationship of Sebaceous Cell Stage to Growth in Culture", *J Invest Dermatol* 92:751–754, 1989.
Schmidt, Endo, Rutledge, Vogel, Shinar, Rodan, *Mol. Endocrinol.*, 6:1634–1641, 1992.
Sherins R J, Bardin C W, *Endocrinol*, 89:835–841, 1971.
Thody A T, Shuster S, *Physiol Rev*, 69:383–415, 1989.
Tontonoz, Hu, Graves, Budavari, Spiegelman, *Genes & Development*, 8:1224–1234, 1994.
Tontonoz, Hu, Spiegelman, *Cell*, 79:1147–1156, 1994.
Wheatley V R, Brind J L, *J Invest Dermatol*, 76:293–296, 1981.
Wheatley V R, *In: Physiology and Pathophysiology of Skin*, Jarrett A., ed. New York: Academic Press, Vol 9, 1986.
Wheatley V R, *J Invest. Dermatol.*, 73:291–296, 1979.
Yarbrough W G, Quarinby V E, Simental J A, Joseph D R-Sar M, Lubahn D B, Olsen K L, French F S, Wilson E M, *J Biol Chem*, 265:8893–8900, 1990.
Zhu, Alvares, Huang, Rao, Reddy, *J Biol. Chem.*, 268:26817–26820, 1993.

What is claimed is:

1. A method for the identification of a candidate inhibitor substance that is an antagonist of sebum formation comprising the steps of:

(a) providing at least one immature sebocyte;

(b) contacting said sebocyte with an androgen composition, a non-androgenic stimulator of sebum formation and a candidate inhibitor substance;

(c) culturing said sebocyte; and (d) comparing the formation of sebum in said sebocyte with the formation of sebum in an immature sebocyte contacted with said androgen composition and said stimulator, but in the absence of said candidate inhibitor substance.

2. The method of claim 1, further comprising a plurality of sebocytes, wherein said culture is a monolayer culture.

3. The method of claim 1, wherein said non-androgen stimulator is a peroxisome proliferator.

4. The method of claim 1, wherein said non-androgen stimulator is a prostaglandin $J_2$ metabolite.

5. The method of claim 1, wherein said non-androgen stimulator is selected from the group consisting of a thiazolidinedione, linoleic acid, growth hormone, troglitazone, pyrinixic acid, tetrazole-substituted acetophenone and clofibrate.

6. The method of claim 1, wherein said androgen composition comprises testosterone, 5α-dihydrotestosterone, ethyltestosterone, dehydroepiandrosterone, dehydroepiandrosterone sulfate, methyltestosterone, androsteredione, androstanediols, estradiol, mibolerone or fluoxymesterone or analogs thereof.

7. The method of claim 1, wherein said androgen composition is dihydrotestosterone.

8. The method of claim 7, wherein the dihydrotestosterone is present in a concentration between about $10^{-5}$M and about $10^{-9}$ M.

9. The method of claim 8, wherein the dihydrotestosterone is present in a concentration of about $10^{-6}$M.

10. The method of claim 1, wherein sebum formation is determined through light microscopy, electron microscopy, fluorescence microscopy or chromatographic techniques.

* * * * *

UNITED STATES PATENT AND TRADEMARK OFFICE
CERTIFICATE OF CORRECTION

PATENT NO.   : 6,004,751
DATED        : December 21, 1999
INVENTOR(S)  : Rosenfield It is certified that error appears in the above-identified patent and that said Letters Patent is hereby corrected as shown below:

Title page,
Item [56], References Cited, insert the following references:
FOREIGN PATENT DOCUMENTS

| | | | | |
|---|---|---|---|---|
| -- | 5,187,175 | 02/16/93 | Belliotti et al. | 03/06/92 |
| | EP 0046597 | 03/03/82 | Europe | |
| | EP 0200443 A1 | 11/05/86 | Europe | |
| | EP 0200443 B1 | 11/05/86 | Europe | |
| | WO 95/04520 | 02/16/95 | PCT | -- |

OTHER PUBLICATIONS, insert the following references:

Akamatsu H, Zouboulis C, Ofanos CE, "Control of Human Sebocyte Proliferation *In Vitro* by Testosterone and 5-Alpha-Dihydrotestosterone Is Dependent on the Localization of the Sebaceous Glands," *J Invest Dermatol*, 99:509-511, 1992.

Akamatsu H, Zouboulis C, Orfanos CE, "Spironolactone Directly Inhibits Proliferation of Cultured Human Facial Sebocytes and Acts Antagonistically to Testosterone and 5α-Dihydrotestosterone *In Vitro*," *J Invest Dermatol*, 100:660-662, 1993.

Alves *et al.*, "Measurement of Lipogensis in Isolated Preputial Gland Cells of the Rat and the Effect of Oestrogen," *J. Endocr.*, 109:1-7, 1986.

Amri, Bonino, Ailhaud, Abumrad, Grimaldi, "Cloning of a Protein That Mediates Transcriptional Effects of Fatty Acids in Preadipocytes," *J. Biol. Chem.*, 270(5):2367-2371, February 1995.

Apfel, Bauer, Crettaz, Forni, Kamber, Kaufmann, LeMotte, Klaus, "A Retinoic Acid Receptor α Antagonist Selectively Counteracts Retinoic Acid Effects," *Proc. Natl. Acad. Sci. USA*, 89:7129-7133, August 1992.

Boris A, Hurley J, Wong CQ, Comai K, Shapiro S, "Sebum-suppressing Activity of the Nonpolar Arotinoid Ro 15-0778 in Rodents," *Arch Dermatol Res*, 280:246-251, 1988.

Brandes, Hertz, Arad, Naishat, Weil, Bar-Tana, "Adipocyte Conversion of Cultured 3T3-L1 Preadipocytes By Bezafibrate," *Life Sci.*, 40:935-941, 1987.

Brind *et al.*, "*In*-vitro Testosterone metabolism in the Mouse Preputial Gland: Intercellular Co-operation and Changes with Cell Maturation," *J. Endocr.*, 100:377-388, 1984.

Brown and Williams, "The rodent preputial gland," *Mammal Review*, 2(4):105-147, December 1972.

Chawla and Lazar, "Peroxisome Proliferator and Retinoid Signaling Pathways Co-regulate Preadipocyte Phenotype and Survival," *Proc. Natl. Acad. Sci. USA*, 91:1786-1790, March 1994.

Chawla, Schwarz, Dimaculangan, Lazar, "Peroxisome Proliferator-Activated Receptor PPAR) γ: Adipose-Predominant Expression and Induction Early In Adipocyte Differentiation," *Endocrinology*, 135(2):798-800, 1994.

Chen, Law, O'Malley, "Identification of Two mPPAR Related Receptors and Evidence for the Existence of Five Subfamily Members," *Biochem. Biophys. Res. Comm.*, 196(2):671-677, October 1993.

Delpassand, Yang, Wallace, Cherif, Quadri, Price, Joubert, Inoue, Podoloff, "Synthesis, Biodistribution, and Estrogen Receptor Scintigraphy of Indium-111-Diethylenetriaminepentaacetic Acid-Tamoxifen Analogue," *J Pharm. Sci.*, 85(6):553-559, June 1996.

UNITED STATES PATENT AND TRADEMARK OFFICE
CERTIFICATE OF CORRECTION

PATENT NO. : 6,004,751
DATED : December 21, 1999
INVENTOR(S) : Rosenfield

It is certified that error appears in the above-identified patent and that said Letters Patent is hereby corrected as shown below:

Dreyer, Krey, Keller, Givel, Helftenbein, Wahli, "Control of the Peroxisomal β-Oxidation Pathway by a Novel Family of Nuclear Hormone Receptors," *Cell*, 68:879-887, March 1992.

Ebling FJ, "The Effects of Cyproterone Acetate and Oestradiol upon Testosterone Stimulated Sebaceous Activity in the Rat," *Acta Endocrinol*, 72:361-365, 1973.

Evans, "The Steroid and Thyroid Hormone Receptor Superfamily," *Science*, 240:889-895, May 1988.

Forman, *et al.*, "15-Deoxy-$\Delta^{12,14}$-Prostaglandin $J_2$ Is A Ligand for the Adipocyte determination Factor PPARγ," *Cell*, 83:803, December 1995.

Fukishima, M., "Biological Activities and Mechanisms of Action of $PGJ_2$ and Related Compounds: An Update," *Prostaglandins Leukotrienrs and Essential Fatty Acids*, 47:1-12, 1992.

Giles and Leff, "The Biology and Pharmacology of Pgd2" *Prostaglandins*, 35(2):277-299, February 1988.

Goldman AS, Katsumata M, Goto MP, "Lipokinins: Novel Phospholipase $A_2$ Activators Mediate Testosterone Effects on Embryonic Genitalia," *J Urol*, 140:1184-1188, November 1988.

Gomez EC, Martinez CA, "Actions of Isotretinoin and Etretinate on the Pilosebaceous Unit," *J Am Acad Dermatol*, 6:746-750, 1982.

Green and Chambon, "Nuclear Receptors Enhance Our Understanding of Transcription Regulation," *TIG.*, 4(11):309-314, November 1988.

International Search Report dated December 12, 1997 (ARCD:216P).

Issemann and Green, "Activation of a Member of the Steroid Hormone Receptor Superfamily by Peroxisome Proliferators," *Nature*, 347:645-650, October 1990.

Jat PS, Noble MD, Ataliotis P, Tanaka Y, Yannoutsos N, Larsen L, Kiousis D, "Direct Derivation of Conditionally Immortal Cell Lines from an H-$2K^b$-tsA58 Transgenic Mouse," *Proc Natl Acad Sci USA*, 88:5096-5100, June 1991.

Kliewer SA, Lenhard JM, Willson TM, *et al.*, "A Prostaglandin $J_2$ Metabolite Binds Peroxisome Proliferator-activated Receptor and Promotes Adipocyte Differentiation," *Cell*, 83:813, December 1995.

Kliewer, Forman, Blumberg, Ong, Borgmeyer, Mangelsdorf, Umesono, Evans, "Differential Expression and Activation of a Family of Murine Peroxisme proliferator-activated Receptors," *Proc. Natl. Acad. Sci. USA*, 91:7355-7359, July 1994.

Latham JAE, Redfern CPF, Thody AJ, de Kretser TA, "Immunohistochemical Markers of Human Sebaceous Gland Differentiation," *J Histochem Cytochem*, 37(5):729-734, 1989.

Laurent SJ, Mednieks MI, Rosenfield RL, "Growth of Sebaceous Cells in Monolayer Culture," *In Vitro Cell Dev Biol*, 28A:83-89, February 1992.

Lehmann, John, Fanjul, Camerson, Lu, Haefner, Dawson, Pfahl, "Retinoids Selective for Retinoid X Receptor Response Pathways," *Science*, 258:1944-1946, December 1992.

Levin, Sturzenbecker, Kazmer, Bosakowski, Huselton, Allenby, Speck, Kratzeisen, Rosenberger, Lovey, Grippo, "9-Cis Retinoic Acid Stereoisomer Binds and Activates the Nuclear Receptor RXRα," *Nature*, 355:359-361, January 1992.

UNITED STATES PATENT AND TRADEMARK OFFICE
CERTIFICATE OF CORRECTION

PATENT NO. : 6,004,751
DATED : December 21, 1999
INVENTOR(S) : Rosenfield

It is certified that error appears in the above-identified patent and that said Letters Patent is hereby corrected as shown below:

Luu-The V, Sugimoto Y, Puy L, Labrie Y, Solache IM, Singh M, Labrie F, "Characterization, Expression, and Immunohistochemical Localization of 5α-Reductase in Human Skin," *J Invest Dermatol*, 102:221-226, 1994.

Mangelsdorf, Ong, Dyck, Evans, "Nuclear Receptor That Identifies a Novel Retinoic Acid Response Pathway," *Nature*, 345:224-229, May 1990.

Mednieks MI, Laurent SJ, Hand AR, Rosenfield RL, "Cyclic AMP-Receptor Protein Activity in Rat Preputial Cells," *J Invest Dermatol*, 97:517-523, 1991.

Mesquita-Guimaraes, Coimbra A, "The Effect of Sexual Hormones on the Lipid and Proteinaceous Secretion of the Rat Preputial Sebaceous Gland,":*Arch Dermatol Res*, 270:325-331, 1981.

Miyake K, Ciletti N, Liao S, Rosenfield RL, "Androgen Receptor Expression in the Preputial Gland and Its Sebocytes," *J Invest Dermatol*, 103:721-725, 1994.

Moll R, Franke WW, Shiller DL, Geiger B, Krepler R, "The Catalog of Human Cytokeratins: Patterns of Expression in Normal Epithelia, Tumors and Cultured Cells," *Cell*, 31:11-24, November 1982.

O'Malley and Conneely, "Orphan Receptors: In Search of a Unifying Hypothesis for Activation," *Mol. Endocrinol.*, 6(9):1359-1361, 1992.

Prottey, C., "Essential Fatty Acids and the Skin," *British Journal of Dermatology*, 94:579-587, 1976.

Rosenfield RL, Miyake K, Ciletti N, Liao S, "Androgen Receptor (AR) and Paradoxical, AR-Dependent, Response to Androgen of Cultured Preputial Sebocytes," *Clin Res*, 41(2):257A, 1993. (Abstract)

Rosenfield RL, "Pilosebaceous Physiology in Relation to Hirsutism and Acne," *Clin Endocrinol Metab*, 15(2):341-362, May 1986.

Rosenfield, R. L., "Preputial Cell Culture as a Model System to Study Sebocyte Development, *Elsevier Science*, 18:41, page 1-5, March 1996.

Rosenfield RL, "Relationship of Sebaceous Cell Stage to Growth in Culture," *J Invest Dermatol*, 92:751-754, 1989.

Rosenfield RL, Deplewski D, "Role of Androgens in the Developmental Biology of the Pilosebaceous Unit," *Am J Med*, 98 (Suppl.1A):80S-88S, January 1995.

Schmidt, Endo, Rutledge, Vogel, Shinar, Rodan, "Identification of a New Member of the Steroid hormone Receptor Superfamily That Is Activated by a Peroxisome Proliferator and Fatty Acids," *Mol. Endocrinol.*, 6:1634-1641, 1992.

Sherins RJ, Bardin CW, "Preputial Gland Growth and Protein Synthesis in the Androgen-Insensitive Male Pseudohermaphroditic Rat," *Endocrinol*, 89(1):835-841, 1971.

Strauss, Pochi, Whitman, "Suppression of Sebaceous Gland Activity with Eicosa-5:8:11:14-Tetraynoic Acid," *Journal of Investigative Dermatology*, 48(5):492-493, 1967.

Thody AT, Shuster S, "Control and Function of Sebaceous Glands," *Physiol Rev*, 69(2):383-415, April 1989.

Tobias and Hamilton, "The Effect of 5,8,11,14,Eicosatetraynoic Acid on Lipid Metabolism," *Lipids*, 14(2):181-193.

Tontonoz, Hu, Graves, Budavari, Spiegelman, "mPPARγ2: Tissue-specific Regulator of an Adipocyte Enhancer," *Genes & Development*, 8:1224-1234, 1994.

Tontonoz, Hu, Spiegelman, "Stimulation of Adipogenesis in Fibroblasts by PPARγ2, a Lipid-activated Transcription Factor," *Cell*, 79:1147-1156, December 1994.

UNITED STATES PATENT AND TRADEMARK OFFICE
CERTIFICATE OF CORRECTION

PATENT NO. : 6,004,751
DATED : December 21, 1999
INVENTOR(S) : Rosenfield

It is certified that error appears in the above-identified patent and that said Letters Patent is hereby corrected as shown below:

Wheatley VR, Brind JL, "Sebaceous Gland Differentiation: III. The Uses and Limitations of Freshly Isolated Mouse Preputial Gland Cells for the *in Vitro* Study of Hormone and Drug Action," *J Invest Dermatol*, 76(4):293-296, 1981.

Yarbrough WG, Quarmby VE, Simental JA, Joseph DR-Sar M, Lubahn DB, Olsen KL, French FS, Wilson EM, "A single Base Mutation in the Androgen Receptor Gene Causes Androgen Insensitivity in the Testicular Feminized Rat," *J Biol Chem*, 265(15):8893-8900, May 1990.

Yu, Bayona, Kallen, Harding, Ravera, McMahon, Brown, Lazar, "Differential Activation of Peroxisome Proliferator-activated Receptors by Eicosanoids," *The Journal of Biological Chemistry*, 270(41):23975-83, October 1995.

Zhu, Alvares, Huang, Rao, Reddy, "Cloning of a new Member of the Peroxisome Proliferator-activated Receptor Gene Family From Mouse Liver," *J. Biol. Chem.*, 268(36):26817-26820, December 1993.

Zouboulis, Akamatsu, Stephanek, Orfanos, "Androgens Affect the Activity of Human Sebocytes in Culture in a Manner Dependent on the Localization of the Sebaceous Glands and Their Effect Is Antagonized by Spironolactone," *Skin Pharmacol.*, 7:33-40, 1994.

Zouboulis, Korge, Akamatsu, Xia, Schiller, Gollnick and Orfanos, "Effects of 13-Cis-Retinoic Acid, All-Trans-Retinoic Acid, and Acitretin on the Proliferation, Lipid Synthesis and Keratin Expression of Cultured Human Sebocytes In Vitro," *Journal of Investigative Dermatology*, 96(5):792-97, 1991.

Signed and Sealed this

Fourteenth Day of September, 2004

JON W. DUDAS
*Director of the United States Patent and Trademark Office*

SEQUENCE LISTING (1) GENERAL INFORMATION:

(iii) NUMBER OF SEQUENCES: 4

```
(2) INFORMATION FOR SEQ ID NO:1:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:1:

AGTCATGGAA CACGGACAGG                                                  20

(2) INFORMATION FOR SEQ ID NO:2:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:2:

CTCCATGTTG AGGCTGCCAC                                                  20

(2) INFORMATION FOR SEQ ID NO:3:

(i) SEQUENCE CHARACTERISTICS:
        (A) LENGTH: 373 base pairs
        (B) TYPE: nucleic acid
        (C) STRANDEDNESS: single
        (D) TOPOLOGY: linear (xi) SEQUENCE DESCRIPTION: SEQ ID NO:3:

CCCAGTGTGA ATTACAGCAA ATCTCTGTTT TATGCTGTTA TGGGTGAAAC TCTGGGAGAT       60
TCTCCTGTTG ACCCAGAGCA TGGTGCCTTC GCTGATGCAC TGCCTATGAG CACTTCACAA      120
GAAATTACCA TGGTTGACAC AGAGATGCCA TTCTGGCCCA CCAACTTCGG AATCAGCTCT      180
GTGGACCTCT CCGTGATGGA AGACCACTCG CATTCCTTTG ACATCAAGCC CTTTACCACA      240
GTTGATTTCT CCAGCATTTC TGCTCCACAC TATGAAGACA TTCCATTCAC AAGAGCTGAC      300
CCAATGGTTC CTGATTACAA ATATGACCTG AAGCTCCAAG AATACCAAAG TGCGATCAAA      360
GTAGAACCTG CAT                                                        373

(2) INFORMATION FOR SEQ ID NO:4:

(i) SEQUENCE CHARACTERISTICS:
        (A) LENGTH: 277 base pairs
        (B) TYPE: nucleic acid
        (C) STRANDEDNESS: single
        (D) TOPOLOGY: linear (xi) SEQUENCE DESCRIPTION: SEQ ID NO:4:

TATGGGTGAA ACTCTGGGAG ATCCTCCTGT TGACCCAGAG CATGGTGCCT TCGCTGATGC       60
ACTGCCTATG AGCACTTCAC AAGAAATTAC CATGGTTGAC ACAGAGATGC CATTCTGGCC      120
CACCAACTTC GGAATCAGCT CTGTGGACCT CTCTGTGATG GATGACAACT CCCAATTCCT      180
TTGACATAAA CCCTTTACCA CGGTTGATTT CTCCACATTT CTGCTCCACA CTATGAAGAC      240
ATCCCGTTCA CAAGAAGCTG ACCCAATGGT TGCTGAT                              277
```